(12) United States Patent
Hayashida et al.

(10) Patent No.: US 7,012,160 B2
(45) Date of Patent: Mar. 14, 2006

(54) FLUORINE-CONTAINING ACETOPHENONE DERIVATIVE, SURFACE LAYER MATERIAL CONTAINING THE SAME AS PHOTO INITIATOR, ARTICLE WITH COMPOSITE HARD COAT LAYER, AND METHOD FOR FORMING COMPOSITE HARD COAT LAYER

(75) Inventors: Naoki Hayashida, Tokyo (JP); Kazushi Tanaka, Tokyo (JP)

(73) Assignee: TDK Corporation, Tokyo (JP)

( * ) Notice: Subject to any disclaimer, the term of this patent is extended or adjusted under 35 U.S.C. 154(b) by 6 days.

(21) Appl. No.: 10/793,268

(22) Filed: Mar. 5, 2004

(65) Prior Publication Data
US 2004/0181087 A1    Sep. 16, 2004

(30) Foreign Application Priority Data
Mar. 12, 2003 (JP) .............................. 2003-067280

(51) Int. Cl.
| | |
|---|---|
| C07C 49/76 | (2006.01) |
| C07C 233/00 | (2006.01) |
| B05D 1/02 | (2006.01) |
| B32B 5/16 | (2006.01) |
| G02C 7/04 | (2006.01) |

(52) U.S. Cl. ...................... 568/335; 568/336; 568/337; 564/161; 564/170; 564/183; 427/447; 428/323; 428/325; 428/331; 351/160; 351/161

(58) Field of Classification Search ................ 568/335, 568/336, 337; 564/161, 170, 183; 427/447; 428/323, 325, 331; 351/160, 161
See application file for complete search history.

(56) References Cited

U.S. PATENT DOCUMENTS 5,147,886 A * 9/1992 Tokizawa et al. ........... 514/383

FOREIGN PATENT DOCUMENTS

| | | |
|---|---|---|
| JP | 6-211945 | 8/1994 |
| JP | 8-508733 | 9/1996 |
| JP | 9-137117 | 5/1997 |
| JP | 2000-301053 | 10/2000 |
| WO | WO 94/22925 | 10/1994 |

OTHER PUBLICATIONS

Yoshino et al. Syntheses of Hybrid Anionic Surfactants Containing Fluorocarbon and Hydrocarbon Chains. Langmuir, 1995, vol. 11, (2), p 466-469.*

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

The present invention provides a new fluorine-containing acetophenone derivative useful as a photo initiator, and a surface layer material containing the fluorine-containing acetophenone derivative. The present invention provides inexpensively an article with a hard coat excellent in antistaining property, lubricity, scratch resistance and abrasion resistance, and provides a method for forming the hard coat. A fluorine-containing acetophenone derivative represented by the following general formula (I):

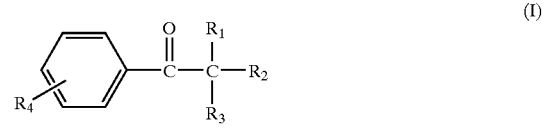

wherein $R_1$, $R_2$ and $R_3$ each independently represent an organic group other than aryl group, a hydrogen atom, a halogen atom or a hydroxyl group, provided that the following case does not take place: all of $R_1$, $R_2$ and $R_3$ are simultaneously hydrogen atoms; and any two of $R_1$, $R_2$ and $R_3$ may be linked to each other to form a ring, and $R_4$ represents a fluorine-containing organic group. Hard coat layer 2 is formed to contact a surface of an article, and a fluorine-containing surface layer 3 using the compound is formed to contact a surface of the hard coat layer 2.

17 Claims, 4 Drawing Sheets

FLUORINE-CONTAINING ACETOPHENONE DERIVATIVE, SURFACE LAYER MATERIAL CONTAINING THE SAME AS PHOTO INITIATOR, ARTICLE WITH COMPOSITE HARD COAT LAYER, AND METHOD FOR FORMING COMPOSITE HARD COAT LAYER

BACKGROUND OF THE INVENTION

1. Field of the Invention

The present invention relates to a new fluorine-containing acetophenone derivative useful as a photo initiator. The present invention relates to a surface layer material containing the fluorine-containing acetophenone derivative as a photo initiator.

The present invention relates to an article with a composite hard coat layer obtained using the surface layer material containing the fluorine-containing acetophenone derivative as a photo initiator, and a method for forming a composite hard coat layer using the surface layer material containing the fluorine-containing acetophenone derivative as a photo initiator. In the present invention, a composite hard coat layer includes a hard coat layer which is formed on a surface of an article and has scratch resistance and abrasion resistance, and a anti-staining surface layer which is formed on the surface of the hard coat layer and has anti-staining property and lubricity. More specifically, the present invention relates to an article having, on a surface thereof, a composite hard coat layer having anti-staining property, lubricity, scratch resistance and abrasion resistance in the field of various articles for which these properties are required, and a method for forming the composite hard coat layer.

In particular, the present invention concerns a method for forming a composite hard coat layer having anti-staining property, lubricity, scratch resistance and abrasion resistance on a surface of an optical recording medium, a magneto-optical recording medium, an optical lens, an optical filter, an anti-reflection film, or any one of various display elements such as a liquid crystal display, a CRT display, a plasma display and an EL display, without deteriorating these optical property and recording property, and also concerns an article on which this hard coat layer is formed.

Furthermore, the present invention relates to an article with a fluorine-containing surface layer obtained using the surface layer material containing the fluorine-containing acetophenone derivative as a photo initiator. The fluorine-containing surface layer provides anti-staining property and lubricity to the surface of the article.

2. Disclosure of the Related Art

Usually, a protective layer (hard coat layer) is given to the surface of various articles for which scratch resistance and abrasion resistance are required, for example, optical recording media such as a CD (Compact Disk) and a DVD (Digital Versatile Disk), magneto-optical recording media, an optical lens, an optical filter, an anti-reflection film, and various display elements such as a liquid crystal display, a CRT display, a plasma display and an EL display.

In many cases, stains such as a fingerprint, sebum, sweat and cosmetics are adhered to the surface of these articles by user's use of the articles. Once such stains are adheres thereto, they are not easily removed. This is a serious problem, in particular, for optical recording media or optical lenses used to record or reproduce the media since the recording and reproducing of information signals are remarkably obstructed by-the adhered stains.

In magneto-optical recording media, a magnetic head runs on an organic protective layer formed on their recording layer. Accordingly, it is required that the abrasion resistance of the protective layer is made high and, simultaneously, the frictional coefficient thereof is made low.

As the method for solving the former problem, suggested are various methods of forming, on the surface of an optical lens or the like, a layer having a nature that stains do not adhere easily to the layer and even if stains adhere to the layer, the stains are easily wiped off, that is, a layer having anti-staining property. Specifically, the following method is adopted in many cases: a method of depositing a layer made of a fluorine-containing compound or a silicone compound on the surface to give water repellency and oil repellency to the surface, thereby improving the anti-staining property.

About the method for overcoming the latter problem, that is, the method for decreasing the frictional coefficient of the surface of a protective layer (hard coat layer), many measures have been suggested so far. Specifically, the following method is used in many cases: a method of depositing, on the surface of the protective layer, a film made of a liquid lubricant such as a fluorine-containing polymer (for example, perfluoropolyether) or a silicone polymer (for example, polydimethylsiloxane), thereby improving lubricity.

Originally, the former anti-staining property and the latter lubricity are entirely different properties. However, it is common to the two that a fluorine-containing compound or a silicone compound is used as means for giving each of these properties in many cases. Accordingly, problems common to the two are frequently caused when a fluorine-containing compound or a silicone compound is used to give anti-staining property or lubricity to the surface of a hard coat.

Many fluorine-containing compounds or silicone compounds are soft. Thus, when these compounds are used, it is very difficult to obtain a sufficient abrasion resistance. In order to overcome such a problem, the following method can be considered: a method of adding an inorganic filler made of $SiO_2$ fine particles or the like to a fluorine-containing polymer or silicone polymer matrix to make the abrasion resistance high. According to such a method, however, a little improvement is made but a satisfactory abrasion resistance cannot be obtained as far as the fluorine-containing polymer or silicone polymer is used as the matrix, wherein the inorganic filler is dispersed.

Therefore, the following method is considered: a method of making a protective layer into a lamination structure composed of two or more different layers, making the lower layer into a layer made of a highly hard material, and depositing an upper layer made of a fluorine-containing compound or silicone compound on the surface thereof, thereby giving anti-staining property or lubricity. In this case, it is preferable to make the upper layer, which is made of the fluorine-containing compound or silicone compound, as thin as possible so as to reflect the hardness of the lower layer in the upper layer, which constitutes the topmost surface of the lamination protective layer. However, in this method, it is very difficult to obtain close adhesion between the lower layer and the upper layer which is made of the fluorine-containing compound or silicone compound.

As the method for solving the above-mentioned problem about the adhesion, for example, the following method is known: a method of forming a lower layer made of an inorganic material such as $SiO_2$ by such a process as sputtering or sol-gel process; forming, on the surface of the lower layer, an upper layer made of alkoxysilane having a fluoroalkyl group by such a process as vapor deposition or solution application; subjecting the resultant to heat treatment in the presence of a very small amount of water content so as to cause dehydration condensation between silanol groups generated by hydrolysis of the alkoxysilane and/or between the silanol groups and hydroxyl groups present in the surface of the lower layer made of $SiO_2$ or the like, whereby the upper layer is fixed onto the lower layer surface through chemical bonds and/or hydrogen bonds.

In this method, it is desired that the lower layer surface has active groups such as hydroxyl groups at a high density. Therefore, the material that can be used in the lower layer is limited to an inorganic material, in particular, a metal oxide or a metal chalcogenide such as $SiO_2$, $Al_2O_3$, $TiO_2$ or ZnS. Even when the lower layer is made of a metal oxide such as $SiO_2$, in order to make adhesion between this metal oxide and the alkoxysilane of the upper layer sufficient, it is necessary to subject the lower layer surface to activating treatment, such as alkali treatment, plasma treatment or corona discharge treatment, for increasing the density of active groups on the surface before the formation of the upper layer.

An attempt is also made for using a lower layer made of an organic material such as polyethylene, polycarbonate or polymethyl methacrylate; making the surface of the lower layer hydrophilic by such a method as plasma treatment or corona discharge treatment; and forming an upper layer made of the same alkoxysilane as described above on the surface of the lower layer. In this case, however, the adhesion is far poorer than in the case that the above-mentioned inorganic material is used as the lower layer. Thus, a sufficient endurance is not obtained.

In the case that a substrate to be hard-coat-treated is made of resin, according to the above-mentioned method in which an inorganic material such as $SiO_2$ is used as the lower layer, it is very difficult to obtain the abrasion resistance of the hard coat. When the layer made of the inorganic material such as $SiO_2$ is deposited on the surface of the resin substrate, the thickness of the film which can be formed is at most about several hundred nanometers. It is difficult from the standpoint of the production process thereof to make the film thickness larger than such a value. Even if such a film can be formed, the inorganic film self-breaks easily since a difference in elastic modulus or thermal expansion coefficient between the inorganic film and the substrate is remarkably large. It is however difficult that the inorganic film having a thickness of several hundred nanometers gives a sufficient abrasion resistance. It is also difficult to obtain a sufficient adhesion between the resin substrate and the inorganic film. Consequently, the inorganic film is easily peeled. From this viewpoint, it is difficult to obtain a sufficient abrasion resistance, as well.

Therefore, in the case that the substrate to be hard-coat-treated is made of resin, it is necessary to deposit a primer layer having a high elastic modulus on the resin substrate, deposit a lower layer made of the same inorganic film as described above on the primer layer, thereby keeping the adhesion between the resin substrate and the inorganic film and the strength of the inorganic film, subject the surface of the lower layer to activating treatment, and form an upper layer made of the same fluorine-containing alkoxysilane as described above on the lower layer surface. Since it is necessary to form the three layers successively in this way, the productivity is very poor.

Japanese Laid-open Patent Publication No. 9-137117 (1997) discloses a method of applying, onto a surface of a resin substrate, a composition comprising a polymerizable compound having in the molecule thereof at least two (meth)acryloyloxy groups and inorganic compound fine particles such as silica fine particles; photo-polymerizing and curing the polymerizable compound by radiation of active energy rays; subjecting the surface of this cured film to corona treatment or plasma treatment; and then applying, onto the treated surface, a silane compound having in the molecule thereof at least one group which can generate a silanol group by hydrolysis, thereby forming a silane compound coat having an improved adhesion to the above-mentioned cured film. In this case, in order to keep the adhesion between the silane compound coat as the upper layer and the cured film as the lower layer, it is likewise necessary to subject the set film surface to corona treatment or plasma treatment.

In the case that about an organic protective layer of the above-mentioned magneto-optical recording medium a liquid lubricant such as perfluoropolyether or polydimethylsiloxane is applied onto the surface of the organic protective layer to form a lubricant film, the adhesion between the organic protective layer and the liquid lubricant film may not be considered very much since the lubricant is a viscous liquid. However, there is a possibility in that the lubricant is decreased by sliding a magnetic field modulating head repeatedly for a long term or the lubricant volatizes little by little in storage of the recording medium over a long term. In this method, therefore, it is desirable that the lubricant is firmly fixed on the organic protective layer surface.

Meanwhile, in order to obtain anti-staining property, it is necessary to give water repellency or oil repellency to the surface of a protective layer, as described above. However, this manner is not necessarily sufficient. The operation of wiping off adhering stains is generally carried out by users. Therefore, in order that users can feel that the operation of wiping off stains is easy at the time of carrying out this operation, it is necessary to decrease the frictional coefficient of the protective layer surface. Relationship between the anti-staining property of an article and the frictional coefficient thereof has hardly been pointed out so far. In reality, however, in order to give anti-staining property, it is essential to make the frictional coefficient low as well as give water repellency and oil repellency.

By making the frictional coefficient of the surface low, an impact caused when a hard projection contacts the surface can be slipped away; therefore, the generation of scratches can be suppressed. Accordingly, from the standpoint of improving the scratch resistance of the hard coat, it is required to make the frictional coefficient of the surface low, as well.

Japanese Laid-open Patent Publication Nos. 6-211945 (1994) and 2000-301053 disclose the formation of a hard coat layer by: applying, onto a substrate, a composition wherein fluoroalkyl acrylate and an acrylic monomer incompatible with this are dissolved at a given ratio in a solvent capable of dissolving the two; and radiating an electron beam onto the composition immediately after the application so as to cure the composition. According to these publications, by the application of the composition into a thickness of 1 to 15 µm and the radiation of the electron beam immediately after the application, the solvent is instantaneously vaporized. Additionally, the fluoroalkyl acrylate compound and the acrylic monomer are localized so that the composition is cured in the state that the fluoroalkyl acrylate is distributed unevenly in the surface of the coat.

However, according to the two publications, it is necessary to radiate the electron beam onto the composition so as to cure the composition instantaneously after the application of the composition and before the uneven distribution based on the volatilization of the solvent because the composition containing the components incompatible with each other is used. Accordingly, the timing of radiating the electron beam after the application is difficult and the method for the application is restricted very much. Coating methods in which the evaporation rate of the solvent is large, for example, spin coating cannot be used.

A most serious problem in the methods disclosed in the publications is that there is a high possibility in that since the solvent is vaporized at the same time when the electron beam is radiated, the solvent in the cured coat cannot be completely removed. In the publications, it is not at all examined whether the solvent is completely removed from the cured coat or not. In the case that a very small amount of the solvent remains inside, no problem is caused immediately after the formation of the hard coat but there is a possibility in that the coat is cracked or peeled after the use of the article with the coat over a long term. The hardness also becomes insufficient. Thus, a warp of the substrate on which the hard coat is formed is apt to increase gradually.

In the method of vaporizing the solvent at the same time when the electron beam is radiated, the cured coat is apt to have a porous structure. Thus, the hardness thereof is insufficient and, further, the optical property may deteriorate. Accordingly, even if no problem is caused in the case of applying this method to the production of familiar articles, it is difficult to apply the method to the production of articles for which a very high optical property is required, for example, an optical lens or an optical recording medium.

In short, a hard coat wherein anti-staining property, lubricity and abrasion resistance are simultaneously realized at high levels has never been known so far.

When a fluorine-containing (meth)acrylate such as fluoroalkyl acrylate is polymerized and cured, radiation of an electron beam or ultraviolet rays can be used. However, an electron beam radiating device is expensive, and it is also necessary to shield the vicinity of the device from X-rays generated from the device. Running costs are also high. From these viewpoints, the ultraviolet ray radiation is more preferable than the electron beam radiation.

In order to polymerize and cure a fluorine-containing (meth)acrylate by ultraviolet ray radiation, it is necessary to add a photo radical initiator thereto so as to obtain a sufficient reactivity. Any fluorine-containing (meth)acrylate is sufficiently soluble in a fluorine-containing solvent such as perfluorocarbon, but any ordinary photopolymerization initiator is insoluble in the same solvent.

Japanese Published Patent Publication No. 8-508733 (1996) discloses a fluorinated photo initiator. However, this fluorinated photo initiator disclosed in this publication is cleaved to generate benzyl radicals. Consequently, the resultant cured coat yellows. It appears that this is based on recombination of the generated radicals with each other. The yellowing is remarkably disadvantageous for articles, such as an optical lens and an optical recording medium, for which a very high optical property is required. Thus, it is difficult to apply the photo initiator causing yellowing to these articles.

SUMMARY OF THE INVENTION

An object of the present invention is to solve the abovementioned problems in the related art and provide a photo radical initiator which is soluble in a fluorine-containing solvent such as perfluorocarbon and has a good compatibility with a fluorine-containing (meth)acrylate compound. An object of the present invention is to provide a surface layer material which causes no yellowing.

An object of the present invention is also to provide inexpensively an article with a hard coat excellent in anti-staining property, lubricity, scratch resistance and abrasion resistance. Still another object of the present invention is to provide a method for forming a hard coat excellent in anti-staining property, lubricity, scratch resistance and abrasion resistance inexpensively and easily.

Further, an object of the present invention is to provide inexpensively an article with a fluorine-containing surface layer excellent in anti-staining property and lubricity.

The present inventors made eager investigation. As a result, the present inventors have found out a new fluorine-containing acetophenone derivative useful as a photo radical initiator, and also found out that a fluorine-containing (meth) acrylate compound and a surface layermaterial containing the fluorine-containing acetophenone derivative as a photo initiator are used for a fluorine-containing surface layer to be cured/made into a hard coat layer having scratch resistance and abrasion resistance on a surface of an article and be cured/made into a fluorine-containing surface layer having anti-staining property and lubricity on the surface of the hard coat layer simultaneously by radiating ultraviolet rays onto the two layers, thereby forming a transparent composite hard coat layer in which the fluorine-containing surface layer and the hard coat layer are firmly adhered to each other. Thus, the present invention has been made.

A first aspect of the present invention is a fluorine-containing acetophenone derivative represented by the following general formula (I):

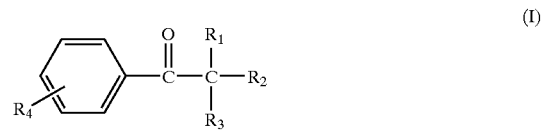

(I)

wherein $R_1$, $R_2$ and $R_3$ each independently represent an organic group other than aryl group, a hydrogen atom, a halogen atom or a hydroxyl group, provided that the following case does not take place: all of $R_1$, $R_2$ and $R_3$ are simultaneously hydrogen atoms; and any two of $R_1$, $R_2$ and $R_3$ may be linked to each other to form a ring, and $R_4$ represents a fluorine-containing organic group.

It is preferable in the first aspect of the present invention that in the general formula (I), the organic groups represented by $R_1$, $R_2$ and $R_3$, none of which are aryl groups, are alkyl groups which may be substituted, alkoxy groups which may be substituted, alkylcarbonyloxy groups which may be substituted, arylcarbonyloxy groups which may be substituted or amino groups.

It is preferable in the first aspect of the present invention that the fluorine-containing organic group represented by $R_4$ in the general formula (I) has at least one fluorine-containing unit selected from the group consisting of:

(a) —[C(X)F]k-;
(b) —[C(X)F—O]l-;
(c) —[C(X)F—C(Y)F—O]m-; and
(d) —[C(X)F—C(Y)F—C(Z)F—O]n-, wherein X, Y and Z each independently represent a F atom or a $CF_3$ group, and k, l, m and n each represent the number of the fluorine-containing units, in such a manner that the total number of the fluorinated carbon atoms contained in the selected fluorine-containing unit is 5 or more.

It is preferable in the first aspect of the present invention that the fluorine-containing organic group represented by $R_4$ in the general formula (I) is an Rfa-L-group, wherein L represents a bivalent linking group, having a perfluoroalkyl group Rfa containing the fluorine-containing unit (a) —[C(X)F]k- ($5 \leq k$).

It is preferable in the first aspect of the present invention that the fluorine-containing organic group represented by $R_4$ in the general formula (I) is an Rfa-COO—$(CH_2)$j-O— group, wherein j is an integer of 2 to 6, or an Rfa-NHCOO—$(CH_2)$j-O— group, wherein j is an integer of 2 to 6, having a perfluoroalkyl group Rfa containing the fluorine-containing unit (a) —[C(X)F]k- ($5 \leq k$).

It is preferable in the first aspect of the present invention that the fluorine-containing organic group represented by $R_4$ in the general formula (I) is an Rfe-L-group, wherein L represents a bivalent linking group, having a perfluoroether-containing group Rfe containing at least one selected from the group consisting of the fluorine-containing units (b) —[C(X)F—O]l-, (c) —[C(X)F—C(Y)F—O]m-, and (d) —[C(X)F—C(Y)F—C(Z)F—O]n-.

It is preferable in the first aspect of the present invention that the fluorine-containing organic group represented by $R_4$ in the general formula (I) is an Rfe-COO—$(CH_2)$j-O— group, wherein j is an integer of 2 to 6, or an Rfe-NHCOO—$(CH_2)$j-O— group, wherein j is an integer of 2 to 6, having a perfluoroether-containing group Rfe containing at least one selected from the group consisting of the fluorine-containing units (b) —[C(X)F—O]l-, (c) —[C(X)F—C(Y)F—O]m-, and (d) —[C(X)F—C(Y)F—C(Z)F—O]n-.

A second aspect of the present invention is a surface layer material comprising a fluorine-containing (meth)acrylate compound and any one of the fluorine-containing acetophenone derivatives as a photo initiator. By using the surface layer material, a composite hard coat layer comprising a hard coat layer on a surface of an article, and a fluorine-containing surface layer on the surface of the hard coat layer can be formed on the surface of the article. By using the surface layer material, a fluorine-containing surface layer, namely a fluorine-containing surface coat also can be formed on the surface of the article.

A third aspect of the present invention is an article with a composite hard coat layer comprising a hard coat layer on a surface of the article, and a fluorine-containing surface layer on the surface of a hard coat layer, wherein the hard coat layer is made of a cured product of a hard coat agent composition comprising an active energy ray-curable compound, and the fluorine-containing surface layer is made of a cured product of a surface layer material comprising a fluorine-containing (meth)acrylate compound and above-mentioned fluorine-containing acetophenone derivative as a photo initiator. The fluorine-containing surface layer is fixed on the hard coat layer. The words "is fixed" means that about the water repellency of the composite hard coat layer as described in Examples, the contact angle of water on the hard coat surface is 85 degrees or more at both of the initial time and the time after a cloth is slid on the surface. If the hard coat layer is not fixed, the contact angle of 85 degrees or more cannot be attained, in particular, after the sliding.

It is preferable in the third aspect of the present invention that the fluorine-containing surface layer has a thickness of 1 nm or more and 100 nm or less.

It is preferable in the third aspect of the present invention that the active energy ray-curable compound comprised in the hard coat agent composition is a compound having at least one reactive group selected from the group consisting of a (meth)acryloyl group, a vinyl group and a mercapto group.

It is preferable in the third aspect of the present invention that the hard coat agent composition comprises a photo initiator and optionally comprises an inorganic filler.

It is preferable in the third aspect of the present invention that the article is an optical recording medium, a magneto-optical recording medium, an optical lens, an optical filter, an anti-reflection film, or a display element. Examples of the display element include a liquid crystal display, a CRT display, a plasma display and an EL display.

A fourth aspect of the present invention is a method for forming a composite hard coat layer comprising a hard coat layer on a surface of an article and a fluorine-containing surface layer, the method comprising the steps of:

applying a hard coat agent composition comprising an active energy ray-curable compound onto a surface of an article to be hard-coat-treated, thereby forming a hard coat agent composition layer, applying, onto the surface of the hard coat agent composition layer, a surface layer material comprising a fluorine-containing (meth)acrylate compound and the above-mentioned fluorine-containing acetophenone derivative as a photo initiator, thereby forming a surface material layer, and radiating ultraviolet rays onto the formed hard coat agent composition layer and surface material layer so as to cure the two layers simultaneously, thereby forming a hard coat layer contacting the surface of the article and a fluorine-containing surface layer contacting the surface of the hard coat layer.

It is preferable in the fourth aspect of the present invention that the fluorine-containing surface layer is formed to have a thickness of 1 nm or more and 100 nm or less.

It is preferable in the fourth aspect of the present invention that after the hard coat agent composition is applied onto the surface of the article, thereby forming the hard coat agent composition layer, the hard coat agent composition layer is dried to remove a solvent contained in the hard coat agent composition from the hard coat agent composition layer, and subsequently the surface layer material is applied onto the surface of the hard coat agent composition layer, thereby forming the surface material layer.

It is preferable in the fourth aspect of the present invention that at the time of applying the surface layer material, there is used, as a solvent, a solvent in which the active energy ray-curable compound in the already-formed hard coat agent composition layer is not substantially dissolved.

It is preferable in the fourth aspect of the present invention that the ultraviolet rays are radiated in an atmosphere having a oxygen concentration of 500 ppm by volume or less.

It is preferable in the fourth aspect of the present invention that after the hard coat agent composition is applied onto the surface of the article, thereby forming the hard coat agent composition layer, the hard coat agent composition layer is dried if necessary; an active energy ray is radiated onto the hard coat agent composition layer to turn this composition layer into a half-cured state; and then the surface material layer is formed on the surface of the hard coat agent composition layer.

A fifth aspect of the present invention is an article with a composite hard layer comprising a hard coat layer on a surface of the article and a fluorine-containing surface layer, wherein the article is obtained by applying a hard coat agent composition comprising an active energy ray-curable com pound onto a surface of an article to be hard-coat-treated, thereby forming a hard coat agent composition layer, applying, onto the surface of the hard coat agent composition layer, a surface layer material comprising a fluorine-containing (meth)acrylate compound and the above-mentioned fluorine-containing acetophenone derivative as a photo initiator, thereby forming a surface material layer, and radiating ultraviolet rays onto the formed hard coat agent composition layer and surface material layer so as to cure the two layers simultaneously, thereby forming a hard coat layer contacting the surface of the article and a fluorine-containing surface layer contacting the surface of the hard coat layer so as to form, on the surface of the article.

In the present invention, the fluorine-containing surface layer provides anti-staining property and lubricity. The fluorine-containing surface layer also provides larger antireflecting property than ordinary resin layers.

In the specification, the wording "a hard coat agent composition layer" means a hard coat layer which has not been cured or has been half-cured (i.e., has been partially cured). The wording "a surface material layer" means a fluorine-containing surface layer which has not been cured. An active energy ray-curable compound is a compound which can be cured by radiation of an active energy ray such as an ultraviolet ray, an electron beam or a visible ray.

A sixth aspect of the present invention is an article with a fluorine-containing surface layer made of a cured product of a surface layer material on a surface of the article, wherein the surface layer material comprises a fluorine-containing (meth)acrylate compound and any one of the fluorine-containing acetophenone derivative as a photo initiator. The article includes the same articles as the above-mentioned articles in this aspect, the fluorine-containing surface layer provides only anti-staining property and lubricity.

According to the present invention, a new fluorine-containing acetophenone derivative is provided. This compound is soluble in a fluorine-containing solvent such as perfluorocarbon, and has a good compatibility with a fluorine-containing (meth)acrylate compound. Thus, the compound is very useful as a radical photo initiator.

According to the present invention, provided is a surface layer material, which causes no yellowing, containing a fluorine-containing (meth)acrylate compound and the fluorine-containing acetophenone derivatives as a photo initiator.

According to the present invention, by using the surface layer material, provided is inexpensively and easily an article with a hard coat which has not only-high scratch resistance and abrasion resistance but also excellent anti-staining property and lubricity, and is also very good in persistence thereof.

Further, according to the present invention, by using the surface layer material, a fluorine-containing surface layer excellent in anti-staining property and lubricity can be formed.

DETAILED DESCRIPTION OF THE INVENTION

Figure 1:
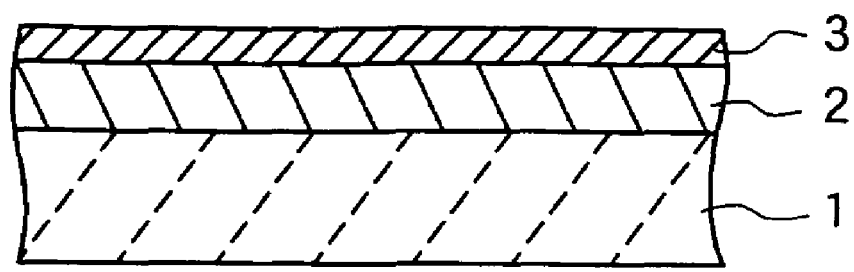
FIG. 1 is a sectional view which schematically illustrates an example of the layer structure of the article with a composite hard coat layer of the present invention.

First, the fluorine-containing acetophenone derivative represented by the general formula (I) will be described.

In the general formula (I), $R_1$, $R_2$ and $R_3$ each independently represent (that is, $R_1$, $R_2$ and $R_3$, which may be the same or different, represent) an organic group other than aryl group, a hydrogen atom, a halogen atom or a hydroxyl group. However, from the viewpoint of the stability of radicals generated by α-cleavage, the following case does not take place: all of $R_1$, $R_2$ and $R_3$ are simultaneously hydrogen atoms. In the molecule, any two of $R_1$, $R_2$ and $R_3$ maybe linked to each other to form a ring. $R_4$ represents a fluorine-containing organic group.

The halogen atoms represented by $R_1$, $R_2$ and $R_3$ maybe fluorine, chlorine, bromine or iodine atoms.

Examples of the organic groups represented by $R_1$, $R_2$ and $R_3$, none of which are aryl groups, may be alkyl groups which may be substituted, alkoxy groups which may be substituted, alkylcarbonyloxy groups which may be substituted, arylcarbonyloxy groups which may be substituted, and an amino group. If any one of $R_1$, $R_2$ and $R_3$ directly becomes an aryl group, benzyl radicals are generated by cleavage when the acetophenone derivative is used as a photo initiator. As a result, intense yellowing is caused in the resultant cured coat. Therefore, none of $R_1$, $R_2$ and $R_3$ directly become aryl groups.

Examples of the alkyl group include methyl, ethyl, propyl, butyl, pentyl and hexyl groups. The alkyl group may have a halogen atom such as a fluorine atom, or may have a substituent such as an alkoxy or aryl group. Any two of $R_1$, $R_2$ and $R_3$ may be linked to each other to form, for example, a cyclohexyl ring.

Examples of the alkoxy group include methyloxy, ethyloxy, propyloxy, butyloxy, pentyloxy and hexyloxy groups. The alkoxy group may have a halogen atom such as a fluorine atom, or may have a substituent such as an alkoxy or aryl group.

Examples of the alkylcarbonyloxy group include methylcarbonyloxy, ethylcarbonyloxy, propylcarbonyloxy, butylcarbonyloxy, pentylcarbonyloxy, and hexylcarbonyloxy. The alkylcarbonyloxy may have a halogen atom such as a fluorine atom, or may have a substituent such as an alkoxy or aryl group. Preferable examples thereof include perfluoroalkylcarbonyloxy groups wherein the total number of fluorinated carbon atoms is 5 or more and 50 or less. In order to obtain a good solubility of perf luorocarbon or the like in a fluorine-containing solvent in this case, the total number of the fluorinated carbon atoms is preferably 5 or more and 50 or less. If the number of the fluorinated carbon atoms is increased to exceed 50, the solubility is not expected to be improved and, additionally, it may be difficult to obtain starting material or synthesize or purify the target compound.

An example of the arylcarbonyloxy group is a phenylcarbonyloxy group. The phenyl group may have one or more of various substituents. An example of the amino group includes a morpholino group.

Apreferable combination of $R_1$, $R_2$ and $R_3$ is not particularly limited. Examples thereof are as follows:

$R_1=R_2=R_3=Cl$;

$R_1=R_2=Cl$, and $R_3=H$;

$R_1$=H, and $R_2$=$R_3$=OC$_2$H$_5$;
$R_1$=OH, and $R_2$=$R_3$=CH$_3$;
$R_1$=OH, and $R_2$ and $R_3$ form a cyclohexyl ring;
$R_1$=$R_2$=CH$_3$, and $R_3$=a morpholino group; and
$R_1$=$R_2$=CH$_3$, and $R_3$=a OCO-perfluoroalkyl group.

In the general formula (I), $R_4$ is a fluorine-containing organic group. $R_4$ contains fluorine, thereby improving the solubility of the acetophenone derivative in a fluorine-containing solvent such as perfluorocarbon and making the compatibility thereof with a fluorine-containing (meth)acrylate compound good.

In the general formula (I), the fluorine-containing organic group represented by $R_4$ may be an organic group having at least one fluorine-containing unit selected from the group consisting of:

(a) —[C(X)F]k-;
(b) —[C(X)F—O]l-;
(c) —[C(X)F—C(Y)F—O]m-; and
(d) —[C(X)F—C(Y)F—C(Z)F—O]n-, wherein X, Y and Z each independently represent a F atom or a CF$_3$ group, and k, l, m and n each represent the number of the fluorine-containing units, in such a manner that the total number of the fluorinated carbon atoms contained in the selected fluorine-containing unit is 5 or more, preferably 50 or less. By setting the total number of the fluorinated carbon atoms into 5 or more and 50 or less, the compound represented by the general formula (I) can have a good solubility in a fluorine-containing solvent such as perfluorocarbon. Even if the number of the fluorinated carbon atoms is increased to exceed 50, the solubility is not expected to be improved and, further, it may be difficult to obtain starting material or synthesize or purify the target compound.

In the general formula (I), a preferable example of the fluorine-containing organic group represented by $R_4$ is an Rfa-L-group, wherein L represents a bivalent linking group, having a perfluoroalkyl group Rfa containing the fluorine-containing unit (a) —[C(X)F]k- (5≦k).

The bivalent linking group L is any group through which group the perfluoroalkyl group Rfa can be linked to the benzene ring in the general formula (I). Various linking groups may be used. Examples thereof include:

(f) —COO—;
(g) —COO—(CH$_2$)j-O—;
(h) —CH$_2$CH(OH)CH$_2$O—;
(i) —CH$_2$CH(OH)CH$_2$O—(CH$_2$)j-O—;
(j) —CH$_2$O—;
(k) —CH$_2$O—(CH$_2$)j-O—;
(l) —(CH$_2$)j-; and
(m) —NHCOO—(CH$_2$)j-O—.

Among these examples, (f) —COO— and (g) —COO—(CH$_2$)j-O— (m) —NHCOO—(CH$_2$)j-O— are preferable. In each of the above-mentioned formulae, —(CH$_2$)j- is preferably a lower alkylene group. That is, j is preferably an integer of 2 to 6.

In the general formula (I), a preferable example of the fluorine-containing organic group represented by $R_4$ is an Rfa-COO—(CH$_2$)j-O— group, wherein j is an integer of 2 to 6, and an Rfa-NHCOO—(CH$_2$)j-O— group, wherein j is an integer of 2 to 6, having a perfluoroalkyl group Rfa which contains the fluorine-containing unit (a) —[C(X)F]k- (5≦k) and has a terminal of F. Examples of the perfluoroalkyl group Rfa include an F(CF$_2$)k- group wherein 5≦k≦50. Examples of the lower alkylene group represented by —(CH$_2$)j- include ethylene, propylene, butylene and hexylene groups, wherein j is from 2 to 6 in the —(CH$_2$)j-.

In the general formula (I), a preferable example of the fluorine-containing organic group represented by $R_4$ is an Rfe-L-group, wherein L represents a bivalent linking group, having a perfluoroether-containing group Rf e which contains at least one selected from the group consisting of the fluorine-containing units (b) —[C(X)F—O]l-, (c) —[C(X)F—C(Y)F—O]m-, and (d) —[C(X)F—C(Y)F—C(Z)F—O]n- and, optionally, contains the fluorine-containing unit (a) —[C(X)F]k-. The bivalent linking group L is the same as described above.

In the general formula (I), a preferable example of the fluorine-containing organic group represented by $R_4$ is an Rfe-COO—(CH$_2$)j-O— group, wherein j is an integer of 2 to 6, and an Rfe-NHCOO—(CH$_2$)j-O— group, wherein j is an integer of 2 to 6, having a perfluoroether-containing group Rfe which contains at least one selected from the group consisting of the fluorine-containing units (b) [C(X)F—O]—, (c) —[C(X)F—C(Y)F—O]m-, and (d) —[C(X)F—C(Y)F—C(Z)F—O]n- and, optionally, contains the fluorine-containing unit (a) —[C(X)F]k-. Examples of the lower alkylene group represented by —(CH$_2$)j- include ethylene, propylene, butylene and hexylene groups, wherein j is from 2 to 6 in the —(CH$_2$)j-.

Preferable examples of the perfluoroether-containing group Rfe include:
CF$_3$O(CF$_2$O)l-group,
CF$_3$CF$_2$(CF$_2$CF$_2$O)m-group,
CF$_3$CF$_2$CF$_2$O[CF(CF$_3$)CF$_2$O]m-group,
CF$_3$CF$_2$CF$_2$(CF$_2$CF$_2$CF$_2$O)n-group,
CF$_3$O—[CF(CF$_3$)CF$_2$O]m-/- (CF$_2$O)l-group,
CF$_3$O—(CF$_2$CF$_2$O)m-/- (CF$_2$O)l-group wherein l, m and n are selected in such a manner that the total number of the fluorinated carbon atoms contained in the perfluoroether-containing group Rfe is 5 or more, preferably 50 or less.

Specific examples of the fluorine-containing organic group $R_4$ include the following:
F(CF$_2$)$_8$COO—, F(CF$_2$)$_9$COO—, F(CF$_2$)$_{10}$COO—, F(CF$_2$)$_{11}$COO—, F(CF$_2$)$_{12}$COO—, F(CF$_2$)$_{13}$COO—, F(CF$_2$)$_{14}$COO—, F(CF$_2$)$_{15}$COO—, F(CF$_2$)$_{16}$COO—, F(CF$_2$)$_{17}$COO—, H(CF$_2$)$_8$COO—, (CF$_3$)$_2$CF(CF$_2$)$_2$CH$_2$CH$_2$COO—, (CF$_3$)$_2$CF(CF$_2$)$_2$COO—, (CF$_3$)$_2$CF(CF$_2$)$_4$CH$_2$CH$_2$COO—, (CF$_3$)$_2$CF(CF$_2$)$_4$COO—, (CF$_3$)$_2$CF(CF$_2$)$_6$CH$_2$CH$_2$COO—, (CF$_3$)$_2$CF(CF$_2$)$_6$COO—, (CF$_3$)$_2$CF(CF$_2$)$_8$CH$_2$CH$_2$COO—, (CF$_3$)$_2$CF(CF$_2$)$_8$COO—, (CF$_3$)$_2$CF(CF$_2$)$_3$CF(CF$_3$)CF$_2$COO—, CF$_3$CF$_2$(CF$_2$CF$_3$O)$_2$CF$_2$COO—, CF$_3$OCF$_2$CF$_2$OCF$_2$COO—, (CF$_3$)$_3$CCF$_2$CF(CF$_3$)CF$_2$COO—, F(CF$_2$)$_5$O[CF(CF$_3$)CF$_2$O]$_2$CF(CF$_3$)COO—, F(CF$_2$)$_3$O[CF(CF$_3$)CF$_2$O]$_3$CF(CF$_3$)COO—, F[CF(CF$_3$)CF$_2$O]$_4$CF(CF$_3$)COO—, CF$_2$O(CF$_2$CF$_2$O)$_2$CF$_2$COO—, CF$_3$CF$_2$(CF$_2$CF$_2$O)$_3$CF$_2$COO—, perfluorocyclohexylcarbonyloxy group (C$_6$F$_{11}$COO—), perfluorodecahydronaphthylcarbonyloxy group (C$_{10}$F$_{17}$COO—),
F(CF$_2$)$_8$COOCH$_2$CH$_2$O—, F(CF$_2$)$_9$COOCH$_2$CH$_2$O—, F(CF$_2$)$_{10}$COOCH$_2$CH$_2$O—, F(CF$_2$)$_{11}$COOCH$_2$CH$_2$O—, F(CF$_2$)$_{12}$COOCH$_2$CH$_2$O—, F(CF$_2$)$_{13}$COOCH$_2$CH$_2$O—, F(CF$_2$)$_{14}$COOCH$_2$CH$_2$O—, F(CF$_2$)$_{15}$COOCH$_2$CH$_2$O—, F(CF$_2$)$_{16}$COOCH$_2$CH$_2$O—, F(CF$_2$)$_{17}$COOCH$_2$CH$_2$O—, H(CF$_2$)$_8$COOCH$_2$CH$_2$O—, (CF$_3$)$_2$CF(CF$_2$)$_2$CH$_2$CH$_2$COOCH$_2$CH$_2$O—, (CF$_3$)$_2$CF(CF$_2$)$_2$COOCH$_2$CH$_2$O—, (CF$_3$)$_2$CF(CF$_2$)$_4$CH$_2$CH$_2$COOCH$_2$CH$_2$O—, (CF$_3$)$_2$CF(CF$_2$)$_4$COOCH$_2$CH$_2$O—, (CF$_3$)$_2$CF(CF$_2$)$_6$CH$_2$CH$_2$COOCH$_2$CH$_2$O—, (CF$_3$)$_2$CF(CF$_2$)$_6$COOCH$_2$CH$_2$O—, (CF$_3$)$_2$CF(CF$_2$)$_8$ $CH_2CH_2COOCH_2CH_2O-$, $(CF_3)_2CF(CF_2)_8COOCH_2CH_2O-$, $(CF_3)_2CF(CF_2)_3CF(CF_3)CF_2COOCH_2CH_2O-$, $CF_3CF_2(CF_2CF_2O)_2CF_2COOCH_2CH_2O-$, $CF_3OCF_2CF_2OCF_2COOCH_2CH_2O-$, $(CF_3)_3CCF_2CF(CF_3)CF_2COOCH_2CH_2O-$, $F(CF_2)_3O[CF(CF_3)CF_2O]_2CF(CF_3)COOCH_2CH_2O-$, $F(CF_2)_3O[CF(CF_3)CF_2O]_3CF(CF_3)COOCH_2CH_2O-$, $F[CF(CF_3)CF_2O]_4CF(CF_3)COOCH_2CH_2O-$, $CF_2O(CF_2CF_2O)_2CF_2COOCH_2CH_2O-$, $CF_3CF_2(CF_2CF_2O)_3CF_2COOCH_2CH_2O-$, 2-(perfluorocyclohexylcarbonyloxy)ethyloxy group ($C_6F_{11}COOCH_2CH_2O-$), 2-(perfluorodecahydronaphthylcarbonyloxy)ethyloxy group ($C_{10}F_7COOCH_2CH_2O-$), $CF_3(CF_2)_8CH_2CH(OH)CH_2O-$, $CF_3(CF_2)_9CH_2CH(OH)CH_2O-$, $CF_3(CF_2)_{10}CH_2CH(OH)CH_2O-$, $CF_3(CF_2)_{11}CH_2CH(OH)CH_2O-$, $CF_3(CF_2)_{12}CH_2CH(OH)CH_2O-$, $CF_3(CF_2)_{13}CH_2CH(OH)CH_2O-$, $CF_3(CF_2)_{14}CH_2CH(OH)CH_2O-$, $CF_3(CF_2)_{15}CH_2CH(OH)CH_2O-$, $CF_3(CF_2)_{16}CH_2CH(OH)CH_2O-$, $CF_3(CF_2)_{17}CH_2CH(OH)CH_2O-$, $(CF_3)_2CF(CF_2)_2CH_2CH(OH)CH_2O-$, $(CF_3)_2CF(CF_2)_4CH_2CH(OH)CH_2O-$, $(CF_3)_2CF(CF_2)_6CH_2CH(OH)CH_2O-$, $(CF_3)_2CF(CF_2)_8CH_2CH(OH)CH_2O-$, $H(CF_2)_8CH_2OCH_2CH(OH)CH_2O-$, $CF_3(CF_2)_8CH_2CH(OH)CH_2OCH_2CH_2O-$, $CF_3(CF_2)_9CH_2CH(OH)CH_2OCH_2CH_2O-$, $CF_3(CF_2)_{10}CH_2CH(OH)CH_2OCH_2CH_2O-$, $CF_3(CF_2)_{11}CH_2CH(OH)CH_2OCH_2CH_2O-$, $CF_3(CF_2)_{12}CH_2CH(OH)CH_2OCH_2CH_2O-$, $CF_3(CF_2)_{13}CH_2CH(OH)CH_2OCH_2CH_2O-$, $CF_3(CF_2)_{14}CH_2CH(OH)CH_2OCH_2CH_2O-$, $CF_3(CF_2)_{15}CH_2CH(OH)CH_2OCH_2CH_2O-$, $CF_3(CF_2)_{16}CH_2CH(OH)CH_2OCH_2CH_2O-$, $CF_3(CF_2)_{17}CH_2CH(OH)CH_2OCH_2CH_2O-$, $(CF_3)_2CF(CF_2)_2CH_2CH(OH)CH_2OCH_2CH_2O-$, $(CF_3)_2CF(CF_2)_4CH_2CH(OH)CH_2OCH_2CH_2O-$, $(CF_3)_2CF(CF_2)_6CH_2CH(OH)CH_2OCH_2CH_2O-$, $(CF_3)_2CF(CF_2)_8CH_2CH(OH)CH_2OCH_2CH_2O-$, $H(CF_2)_8CH_2OCH_2CH(OH)CH_2OCH_2CH_2O-$, $F(CF_2)_8O-$, $F(CF_2)_9O-$, $F(CF_2)_{10}O-$, $F(CF_2)_{11}O-$, $F(CF_2)_{12}O-$, $F(CF_2)_{13}O-$, $F(CF_2)_{14}O-$, $F(CF_2)_{15}O-$, $F(CF_2)_{16}O-$, $F(CF_2)_{17}O-$, $H(CF_2)_8O-$, $CF_3(CF_2)_7CH_2CH_2O-$, $CF_3(CF_2)_8CH_2CH_2O-$, $CF_3(CF_2)_9CH_2CH_2O-$, $CF_3(CF_2)_{10}CH_2CH_2O-$, $(CF_3)_2CF(CF_2)_4CH_2CH_2O-$, $(CF_3)_2CF(CF_2)_4O-$, $(CF_3)_2CF(CF_2)_6CH_2CH_2O-$, $(CF_3)_2CF(CF_2)_6O-$, $(CF_3)_2CF(CF_2)_8CH_2CH_2O-$, $(CF_3)_2CF(CF_2)_8O-$, $CF_3CF_2(CF_2CF_2O)_2CF_2O-$, $CF_3CF_2(CF_2CF_2O)_3CF_2O-$, $CF_3O(CF_2CF_2O)_2CF_2O-$, $F(CF_2)_8OCH_2CH_2O-$, $F(CF_2)_9OCH_2CH_2O-$, $F(CF_2)_{10}OCH_2CH_2O-$, $F(CF_2)_{11}OCH_2CH_2O-$, $F(CF_2)_{12}OCH_2CH_2O-$, $F(CF_2)_{13}OCH_2CH_2O-$, $F(CF_2)_{14}OCH_2CH_2O-$, $F(CF_2)_{15}OCH_2CH_2O-$, $F(CF_2)_{16}OCH_2CH_2O-$, $F(CF_2)_{17}OCH_2CH_2O-$, $H(CF_2)_8OCH_2CH_2O-$, $CF_3(CF_2)_7CH_2CH_2OCH_2CH_2O-$, $CF_3(CF_2)_8CH_2CH_2OCH_2CH_2O-$, $CF_3(CF_2)_9CH_2CH_2OCH_2CH_2O-$, $CF_3(CF_2)_{10}CH_2CH_2OCH_2CH_2O-$, $(CF_3)_2CF(CF_2)_4CH_2CH_2OCH_2CH_2O-$, $(CF_3)_2CF(CF_2)_4OCH_2CH_2O-$, $(CF_3)_2CF(CF_2)_6CH_2CH_2OCH_2CH_2O-$, $(CF_3)_2CF(CF_2)_6OCH_2CH_2O-$, $(CF_3)_2CF(CF_2)_8CH_2CH_2OCH_2CH_2O-$, $(CF_3)_2CF(CF_2)_8OCH_2CH_2O-$, $CF_3CF_2(CF_2CF_2O)_2CF_2OCH_2CH_2O-$, $CF_3CF_2(CF_2CF_2O)_3CF_2OCH_2CH_2O-$, $CF_3O(CF_2CF_2O)_2CF_2OCH_2CH_2O-$, The fluorine-containing acetophenone derivative represented by the general formula (I) can be synthesized according to, for example, the following reaction equations:

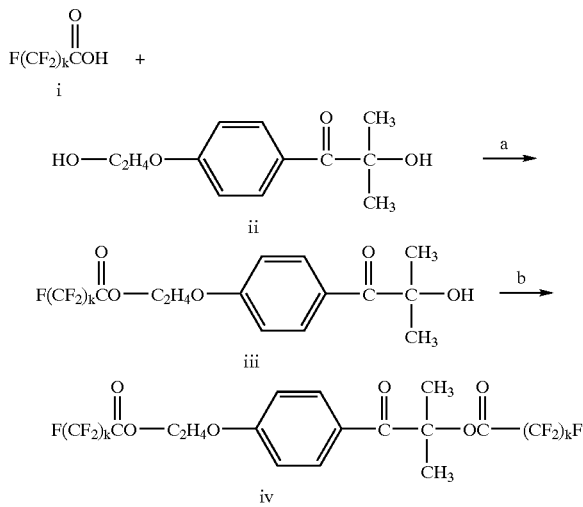

When one equivalent of a perfluoro fatty acid (i) (for example, $5 \leq k$) is caused to react selectively with one equivalent of an acetophenone derivative (ii) (commercially available product: IRGACURE 2959) (route a), a fluorine-containing acetophenone derivative (iii) in which one perfluoroalkyl group is introduced is yielded. When two equivalents of a perfluoro fatty acid (i) is caused to react selectively with one equivalent of an acetophenone derivative (ii) (route b), a fluorine-containing acetophenone derivative (iv) in which two perfluoroalkyl groups are introduced is yielded. The esterification at this time is conducted in a usual way.

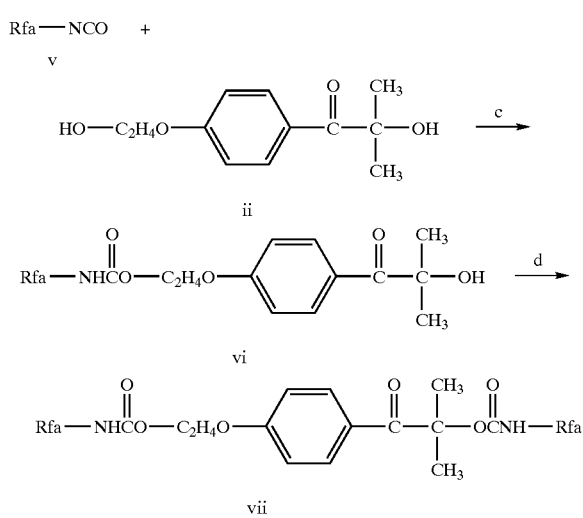

When one equivalent of a perfluoroalkylisocyanate(v) is caused to react selectively with one equivalent of an acetophenone derivative (ii) (commercially available product: IRGACURE 2959) (route c), a fluorine-containing acetophenone derivative (vi) in which one perfluoroalkyl group is introduced is yielded. When two equivalents of a perfluoroalkylisocyanate (v) is caused to react selectively with one equivalent of an acetophenone derivative (ii) (route d), a fluorine-containing acetophenone derivative (vii) in which two perfluoroalkyl groups are introduced is yielded. The urethanization at this time is conducted in a usual way.

In the case that perfluoroetherisocyanate(Rfe-NCO) is used, the fluorine-containing acetophenone derivative in which one perfluoroalkyl group is introduced or the fluorine-containing acetophenone derivative in which two perfluoroalkyl groups are introduced is selectively yielded through the same reaction.

In this way, various fluorine-containing acetophenone derivatives can be synthesized.

The following describes the article with a composite hard coat layer of the present invention and a method for forming the article in detail with reference to FIG. 1.

FIG. 1 is a sectional view which schematically illustrates an example of the layer structure of the article with a composite hard coat layer of the present invention. In FIG. 1, a hard coat layer 2 is formed on a surface of an article 1 to be hard-coat-treated, and a fluorine-containing surface layer 3 is formed to contact the surface of the hard coat layer 2. The combination of the hard coat layer 2 and the fluorine-containing surface layer 3 is referred to as the composite hard coat layer for the sake of convenience.

Examples of the article 1 include various objects for which hard coat treatment is necessary. Specific examples thereof include sheets or substrates made of a thermoplastic resin such as polyethylene terephthalate (PET), polymethyl methacrylate, polyethylene, polypropylene and polycarbonate. However, the article 1 is not limited to these examples. More specific examples of the article include an optical recording medium, a magneto-optical recording medium, an optical lens, an optical filter, an anti-reflection film, and various display elements such as a liquid crystal display, a CRT display, a plasma display and an EL display.

First, a hard coat agent composition containing an active energy ray-curable compound is applied onto a surface of the article 1 so as to form a hard coat agent composition layer. Next, a surface layer material containing a fluorine-containing (meth)acrylate compound and a fluorine-containing acetophenone derivative of the present invention as a photo initiator is applied onto the surface of the hard coat agent composition layer so as to form a surface material layer. The following describes respective components of the hard coat agent composition and the surface layer material.

The active energy ray-curable compound contained in the hard coat agent composition is any compound having at least one active group selected from a (meth)acryloyl group, a vinyl group and a mercapto group. The structure of this compound is not particularly limited. The active energy ray-curable compound preferably contains a polyfunctional monomer or oligomer containing, in the single molecule thereof, 2 or more, preferably 3 or more polymerizable groups in order to give a sufficient hardness to a hard coat.

Among such active energy ray polymerizable compounds, examples of the compound having a (meth)acryloyl group include 1,6-hexanediol di(meth)acrylate, triethylene glycol di(meth)acrylate, ethylene oxide modified bisphenol A di(meth)acrylate, trimethylolpropane tri(meth)acrylate, pentaerythritol tetra(meth)acrylate, ditrimethylolpropane tetra (meth)acrylate, dipentaerythritol hexa(me.th)acrylate, pentaerythritol tri(meth)acrylate, 3-(meth)acryloyloxyglycerin mono(meth)acrylate, urethane acrylate, epoxy acrylate, and ester acrylate. However, the compound having a (meth) acryloyl group is not limited to these examples.

Examples of the compound having a vinyl group include ethylene glycol divinyl ether, pentaerythritol divinyl ether, 1, 6-hexanediol divinyl ether, trimethylolpropane divinyl ether, ethylene oxide modified hydroquinone divinyl ether, ethylene oxide modified bisphenol A divinyl ether, pentaerythritol trivinyl ether, dipentaerythritol hexavinyl ether, and ditrimethylolpropane polyvinyl ether. However, the compound having a vinyl group is not limited to these examples.

Examples of the compound having a mercapto group include ethylene glycol bis(thioglycolate), ethylene glycol bis (3-mercaptopropionate), trimethylolpropane tris(thioglycolate), trimethylolpropane tris(3-mercaptopropionate), pentaerythritol tetrakis(mercaptoacetate), pentaerythritol tetrakis(thioglycolate), and pentaerythritol tetrakis (3-mercaptopropionate). However, the compound having a mercapto group is not limited to these examples.

The active energy ray-curable compounds contained in the hard coat agent composition may be used alone or in combination of two or more thereof.

The hard coat agent composition contains a photopolymerization initiator. The photopolymerization initiator is not particularly necessary when an electron beam is used as the active energy ray. However, when ultraviolet rays are used, the initiator is necessary. As the photopolymerization initiator, any known one can be used. Examples of a radical photo initiator, among the photopolymerization initiators, include a DAROCURE 1173, an IRGACURE 651, an IRGACURE 184, and an IRGACURE 907 (all of which are products manufactured by Ciba Specialty Chemical Inc.). The content by percentage of the photopolymerization initiator is, for example, from about 0.5 to 5% by weight of the hard coat composition (as a solid content).

The hard coat agent composition may contain, as the photopolymerization initiator, the fluorine-containing acetophenone derivative of the present invention instead of or together with the above-mentioned known photopolymerization initiator.

If necessary, the hard coat agent composition may contain an inorganic filler in order to improve the abrasion resistance. Examples of the inorganic filter include silica, alumina, zirconia and titania. The average particle size of the inorganic filler is preferably 100 nm or less, more preferably 50 nm or less in the case that transparency is particularly necessary.

In order to enhance the strength and the abrasion resistance of the cured coat, the surface of the inorganic filler is preferably modified with a compound having an active energy ray polymerizable group. The inorganic filler which has an average particle size of 50 nm or less and is surface-modified with a compound having an active energy ray polymerizable group maybe made of reactive silica particles described in, for example, Japanese Laid-open Patent Publication Nos. 11-60235 (1999), 9-100111(1997) and 2001-187812. This filler is preferably used in the present invention. The silica particles described in Japanese Laid-open Patent Publication No. 11-60235 (1999) contain a cation-reactive oxetanyl group as a reactive group, and the silica particles described in Japanese Laid-open Patent Publication No. 9-100111 (1997) contain a radical-reactive (meth)acryloyl group as a reactive group. The silica particles described in Japanese Laid-open Patent Publication No. 2001-187812 contain both of a radical-reactive unsaturated double bond of a (meth)acryloyl group or the like, and a cation-reactive group of an epoxy group or the like. The addition of such an inorganic filler to the hard coat composition makes it possible that the abrasion resistance of the hard coat layer is made higher. The content by percentage of the inorganic filler is, for example, from about 5 to 80% by weight of the hard coat agent composition (as a solid content). If the content of the inorganic filler is more than 80% by weight, the film strength of the hard coat layer tends to become weak.

If necessary, the hard coat agent composition may further contain a non-polymerizable diluting solvent, a photopolymerization initiator aid, an organic filler, a polymerization inhibitor, an antioxidant, an ultraviolet ray absorber, a photostabilizer, an antifoamer, a leveling agent, a pigment, a silicon compound and others. Examples of the non-polymerizable diluting solvent include isopropyl alcohol, n-butyl alcohol, methyl ethyl ketone, methyl isobutyl ketone, isopropyl acetate, n-butyl acetate, ethylcellosolve, and toluene.

The surface layer material contains a fluorine-containing (meth)acrylate compound and a fluorine-containing acetophenone derivative of the present invention as a photo initiator. The cured coat of this surface layermaterial has at least one function of anti-staining property, lubricity and anti-reflectivity, and is not colored into yellow or the like by the fluorine-containing groups thereof.

Examples of the fluorine-containing (meth)acrylate compound include fluorinated acrylates such as 2,2,3,3,3-pentafluoropropyl (meth)acrylate, 2,2,3,3-tetrafluoropropyl (meth)acrylate, 2,2,2-trifluoroethyl (meth)actylate, 1H,1H, 5H-octafluoropentyl (meth)acrylate, 3-(perfluoro-5-methylhexyl)-2-hydroxypropyl (meth)acrylate, 2-(perfluorooctyl) ethyl acrylate, 3-perfluorooctyl-2-hydroxypropyl (meth) acrylate, 2-(perfluorodecyl)ethyl (meth)acrylate, 2-(perfluoro-9-methyloctyl)ethyl (meth)acrylate, 3-(perfluoro-7-methyloctyl)ethyl (meth)acrylate, 2-(perfluoro-9-methyldecyl)ethyl (meth)acrylate, and 1H,1H,9H-hexadecafluorononyl (meth)acrylate. However, the fluorine-containing (meth)acrylate compound is not limited to these examples. For example, it is also preferable to use a polymer such as perfluoropolyether into which a (meth)acrylate group is introduced, a fluorine-containing compound having a vinyl or mercapto group instead of a (meth)acrylate group, or some other compound. Specific examples thereof include diacrylate of a Fomblin Z DO1 (an alcohol-modified perfluoropolyether product manufactured by Ausimont Co.), and a FLUOLITE ART3 and a FLUOLITE ART4 (products manufactured by Kyoeisha Chemical Co., LTD.).

The fluorine-containing (meth)acrylate compounds may be used alone or in combination of two or more selected from such compounds as described above. The surface layer material may contain, as a part of the components thereof, the active energy ray-curable compound used in the above-mentioned hard coat agent composition.

The fluorine-containing acetophenone derivatives of the present invention may be used alone or in combination of two or more selected from such compounds as described above as a photo initiator or photo initiators.

As a solvent for the surface layer material, a solvent in which the fluorine-containing (meth)acrylate compound can be satisfactorily dissolved is used. For example, a fluorine-containing solvent is preferably used. Examples thereof include fluorocarbons such as perfluorohexane, perfluoroheptane, and perfluorooctane; methyl perf luorobutyl ether; ethyl perfluorobutyl ether; HFC 43-10mee; and 1,1,2,2,3,3, 4-heptafluorocyclopentane. The fluorine-containing acetophenone derivative of the present invention is satisfactorily dissolved in these fluorine-containing solvents, and has good compatibility with the fluorine-containing (meth) acrylate compound. Thus, the derivative is suitable as a photo initiator.

In the same manner for the hard coat agent composition, the surface layer material may contain a non-polymerizable diluting solvent, a photopolymerizable initiator aid, an organic filler, an inorganic filler, a polymerization inhibitor, an antioxidant, an ultraviolet ray absorber, a photo-stabilizer, an antifoamer, a leveling agent, a pigment, a silicon compound and others if necessary.

In the present invention, the above-mentioned hard coat agent composition is first applied onto the surface of the article 1 to form a hard coat agent composition layer. The coating method for the application is not limited, and may be any one of various coating methods such as spin coating, dip coating and gravure coating methods.

After the hard coat agent composition is applied onto the surface of the article 1 and before the surface layer material is applied, it is preferable to remove the fluidity of the hard coat agent composition layer. The removal of the fluidity of the hard coat agent composition layer makes it possible to prevent a variation in the thickness of the hard coat agent composition layer or a deterioration in the surface flatness thereof when the surface layermaterial is applied onto this composition layer. In this way, the surface layermaterial can easily be applied/made into a uniform film.

To remove the fluidity of the hard coat agent composition layer, for example, in the case that a diluting agent is contained in the hard coat agent composition, it is advisable to dry, after the application of the composition, the applied layer so as to remove the solvent contained in the composition from the hard coat agent composition layer. It is also allowable to radiate, after the application and optional drying of the applied layer, an active energy ray such as an ultraviolet ray onto the layer so as to turn the hard coat agent composition layer into a half-cured state. Attention should be paid to the radiation of the active energy ray so as not to cure the hard coat agent composition layer completely. The word "half-cured" means that a part of the applied hard coat agent composition has not yet reacted. Accordingly, the physical hardness of the hard coat agent composition layer is not limited. Thus, the tackiness of the surface is allowed to be lost. The radiation amount of the ultraviolet ray at this time, which depends on the thickness of the hard coat layer, is for example, from 1 to 500 mJ/cm$^2$, preferably from 1 to 200 mJ/cm$^2$. The ultraviolet ray radiation amount of such a degree makes it possible that the hard coat agent composition layer is easily made into a half-cured state.

The thickness of the hard coat layer obtained by curing the hard coat agent composition layer is not particularly limited, and may be appropriately decided in accordance with the kind or the use of the article. In the case that the article is, for example, an optical recording disk, it is advisable to set the thickness into 1 $\mu$m or more and 10 $\mu$m or less, preferably 1 $\mu$m or more and 5 $\mu$m or less. If the thickness is less than 1 $\mu$m, a sufficient surface hardness cannot be give to the disk. If the thickness exceeds 10 $\mu$m, the disk tends to be cracked or largely warped.

Next, the above-mentioned surface layer material is applied onto the surface of the hard coat agent composition layer which has not been cured or which has been partially cured (i.e., which is in the half-cured state) to form a surface material layer. It is advisable to form the surface material layer in such a manner that the thickness of a fluorine-containing surface layer obtained after the surface material layer is cured will be made into 1 nm or more and 100 nm or less, preferably 5 nm or more and 50 nm or less. If the thickness is less than 1 nm, effects of anti-staining property and lubricity are not sufficiently obtained. If the thickness exceeds 100 nm, the hardness of the underlying hard coat layer is not sufficiently reflected. Thus, effects of scratch resistance and abrasion resistance decrease.

The surface layer material is applied by diluting the surface layer material with a suitable diluent and then applying the resultant coating solution by any one of various methods such as spin coating, dip coating, gravure coating, and spray coating methods. After the application, the resultant layer is preferably heated and dried. By this heating and drying treatment, the solvent evaporates and, further, the surface layer material is leveled by heat so that a flat and smooth surface can easily be obtained.

It is preferred to use, as the solvent in this case, a solvent in which the active energy ray-curable compound in the hard coat agent composition layer which has not been cured or has been partially cured is not substantially dissolved. It depends on not only the kind of the solvent but also the coating method whether or not the hard coat agent composition layer is substantially dissolved. In many cases in which as the coating method of the surface material layer, for example, spin coating is used, almost all of the diluting solvent contained in the coating solution volatilizes when the spin coating is performed. Therefore, even if a solvent in which the hard coat agent composition layer is dissolved to some degree is used as the diluting solvent, no practical problems are caused. In the case that as the coating method of the surface material layer, for example, dip coating is used, the hard coat agent composition layer surface which has not been cured contacts the surface material layer coating solution for a long time. It is therefore necessary to use a solvent in which the hard coat agent composition layer material is not at all dissolved or is hardly dissolved.

The solvent which can be used in dip coating is preferably a fluorine-containing solvent. Examples thereof include fluorocarbons such as perfluorohexane, perfluoroheptane and perfluorooctane. A saturated hydrocarbon solvent such as n-octane or isooctane may be used together to such an extent that the solubility of the fluorine-containing (meth) acrylate compound is not damaged. Examples of the solvent which can be used in spin coating include methyl perfluorobutyl ether, ethyl perfluorobutyl ether, HFC 43-10 mee, and 1,1,2,2,3,3,4-heptafluorocyclopentane besides the above-mentioned various solvents. It is allowable to use a solvent such as isopropyl alcohol, n-butyl alcohol, dibutyl ether, ethylcellosolve, or butyl cellosolve to such an extent that the solubility of the fluorine-containing (meth)acrylate compound is not damaged.

In this way, the hard coat agent composition layer which has not been cured or has been partially cured and the surface material layer which is positioned on the surface thereof and has not been cured are formed.

Next, the formed hard coat agent composition layer and surface material layer are irradiated with ultraviolet rays so as to be simultaneously cured. At this time, the ultraviolet rays having an energy amount sufficient to cure the two layers completely are radiated to complete the curing reaction of the two layers. At this time, the radiation amount of the ultraviolet rays is, for example, from 100 to 5000 mJ/cm$^2$, preferably from 500 to 3000 mJ/cm$^2$. By curing, at the same time, the hard coat agent composition layer which has not been cured or has been partially cured and the surface material layer which is formed to contact the surface thereof and has not been cured, the two layers are firmly adhered to each other in the interface therebetween. That is, the cured fluorine-containing surface layer 3 adhered firmly onto the cured hard coat layer 2 is obtained.

By use of such a process of the present invention, it is possible to form, on the high-hardness hard coat layer 2, the fluorine-containing surface layer 3 which is so thin as to reflect the hardness thereof on the topmost surface and is good in water repellency and lubricity and, further, it is possible to obtain good adhesion between the hard coat layer 2 and the fluorine-containing surface layer 3.

As the means for curing the hard coat agent composition layer and the surface material layer simultaneously, ultraviolet rays are used. To set the thickness of the fluorine-containing surface layer into a very small value, such as a value of 1 nm or more and 100 nm or less, preferably 5 nm or more and 50 nm or less and obtain better adhesion of the surface layer to the hard coat layer, it is preferable in the present invention to conduct purging with inactive gas such as nitrogen in such a manner that the oxygen concentration in the atmosphere for the ultraviolet ray radiation will be 500 ppm by volume or less, preferably 200 ppm by volume or less and more preferably 10 ppm by volume or less. This is because the hindrance of the surface-curing, resulting from oxygen radicals generated in the radiation atmosphere, is suppressed. Alternatively, known various oxygen-hindrance inhibitors may be added to the hard coat agent composition and/or the surface layer material instead of the control of the oxygen concentration in the radiation atmosphere. Examples of such an oxygen-hindrance inhibitor include oxygen-hindrance inhibitors described in Japanese Laid-open Patent Publication Nos. 2000-109828, 2000-109828 and 2000-144011. Needless to say, it is allowable to use both of the oxygen-hindrance inhibitor and the control of the oxygen concentration in the radiation atmosphere.

By use of such materials and such film-forming and film-curing methods, there is formed a composite hard coat layer which is excellent in abrasion resistance, water repellency and lubricity and is also good in persistence of these properties.

EXAMPLES

The present invention will be described more specifically by way of the following examples. However, the present invention is not limited to these examples.

Example 1

Synthesis of Fluorine-Containing Photo Initiator A

Into a 300 mL round-bottomed flask with a stirrer were charged 40 g of perfluorononanoic acid (compound i in the above-mentioned reaction equation; k=8) and 6.4 g of 2-hydroxy-4'-(2-hydroxyethoxy)-2-methylpropiophenone (compound ii in the reaction equation), and the mixture was heated to 110° C. When the whole of the starting materials were turned into a melting state, the reaction system was started to be slowly stirred. The reaction was then continued for 4 hours. After the reaction, the reactant was once cooled to room temperature. It was then identified by gas chromatographic analysis that 2-hydroxy-4'-(2-hydroxyethoxy)-2-methylpropiophenone was not present. Furthermore, the reactant was heated to 100 to 160° C. under reduced pressure so as to distill off remaining perfluorononanoic acid. The reactant was again cooled to room temperature to yield about 12 g of a white solid.

The resultant white solid was analyzed by infrared spectroscopy, gel permeation chromatography, gas chromatography, gas chromatographic mass spectroscopy, and so on. As a result, it was identified that a target fluorine-containing photo initiator A, 2-hydroxy-4'-( 2-perfluorononanoyloxyethoxy)-2-methylpropiophenone (compound iii in the reaction equation; k=8) was obtained as a main product. This white solid was used as the fluorine-containing photo initiator A in examples described hereinafter.

Figure 2:
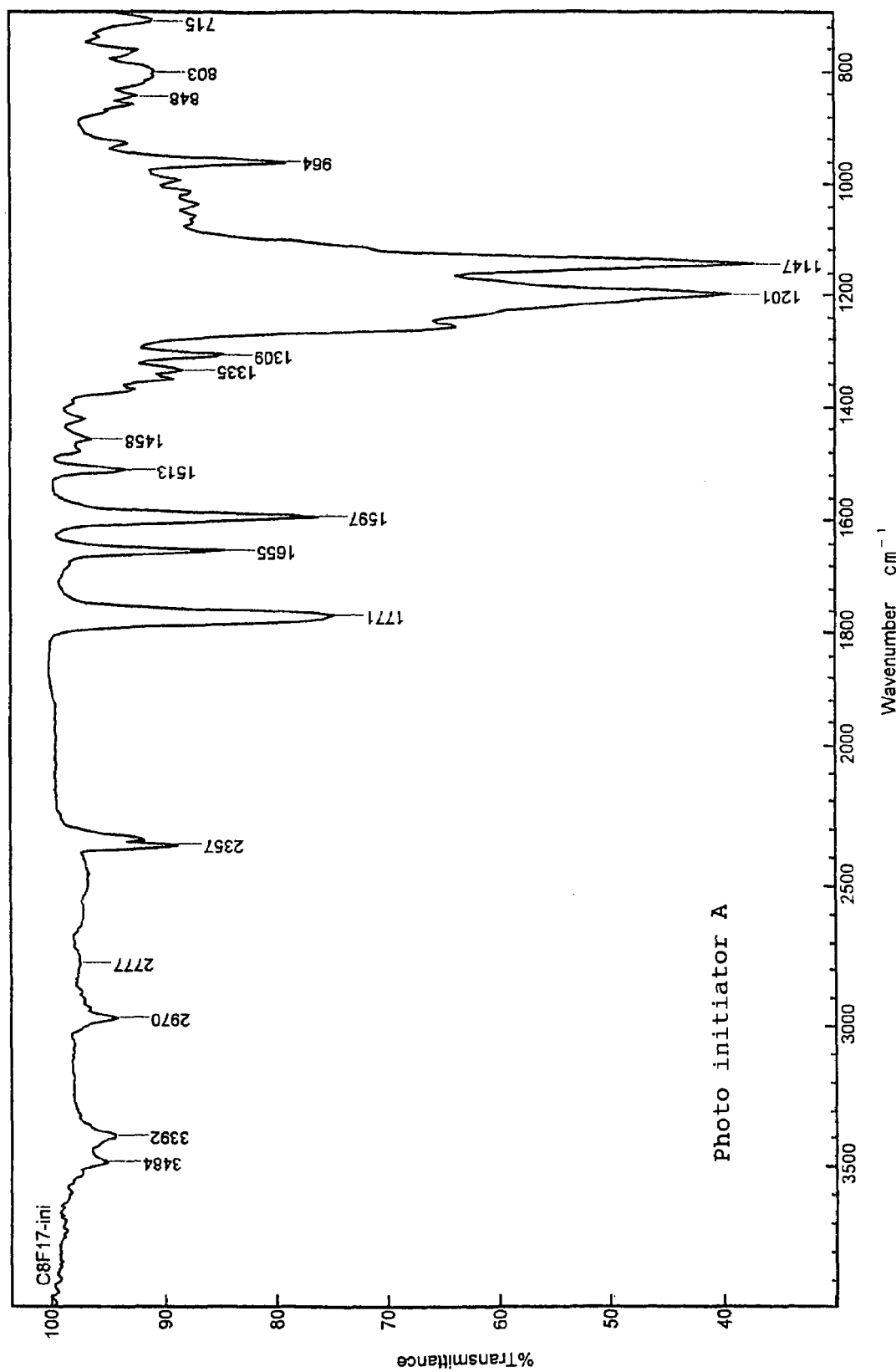
FIG. 2 is an IR chart of a fluorine-containing photo initiator A.

Identification Data on the Photo Initiator A:
IR (FIG. 2): O—H stretch at 3390–3500 cm$^{-1}$;
ester C=O stretch near 1770 cm$^{-1}$;
benzyl position C=O stretch near 1650 cm$^{-1}$;
benzene ring C=C stretch near 1600 cm$^{-1}$; and
perfluoroalkyl group C–F stretch near 1100–1200 cm$^{-1}$.

The white solid was dissolved into perfluorooctane, and the ultraviolet absorption spectrum thereof was measured. As a result, an absorption originating from π–π* transition of the benzene ring of the target product was observed near a wavelength of 260 nm and an absorption originating from n-π* transition of the carbonyl of the benzoyl moiety of the target product was observed in the vicinity of a wavelength of 320 nm. A small amount of 2-(perfluorooctyl)ethyl acrylate was further added to this solution, and ultraviolet rays were radiated onto the solution. As a result, the absorption near 260 nm was largely reduced to suggest advance of the cleavage of the initiator and the addition thereof to the acrylate. Accordingly, from this viewpoint, it was also confirmed that the resultant white solid was made mainly of the target fluorine-containing photo initiator A, 2-hydroxy-4'-(2-perfluorononanoyloxyethoxy)-2-methylpropiophenone (compound iii in the reaction equation; k=8).

Example 2

Synthesis of Fluorine-Containing Photo Initiator B

A reaction was conducted in the same way as in Example 1 expect that 48 g of perfluoroundecanoic acid (k=11) was used instead of 40 g of perfluorononanoic acid (k=8). In this way, about 20 g of a brown solid material was obtained. This material was analyzed in the same way as in Example 1, so that it was identified that a target photo initiator B, 2-hydroxy-4'-(2-perfluoroundecanoyloxyethoxy)-2-methylpropiophenone (compound iii in the reaction equation; k=11) was obtained as a main product. This brown solid material was used as the fluorine-containing photo initiator B in examples described hereinafter.

Figure 3:
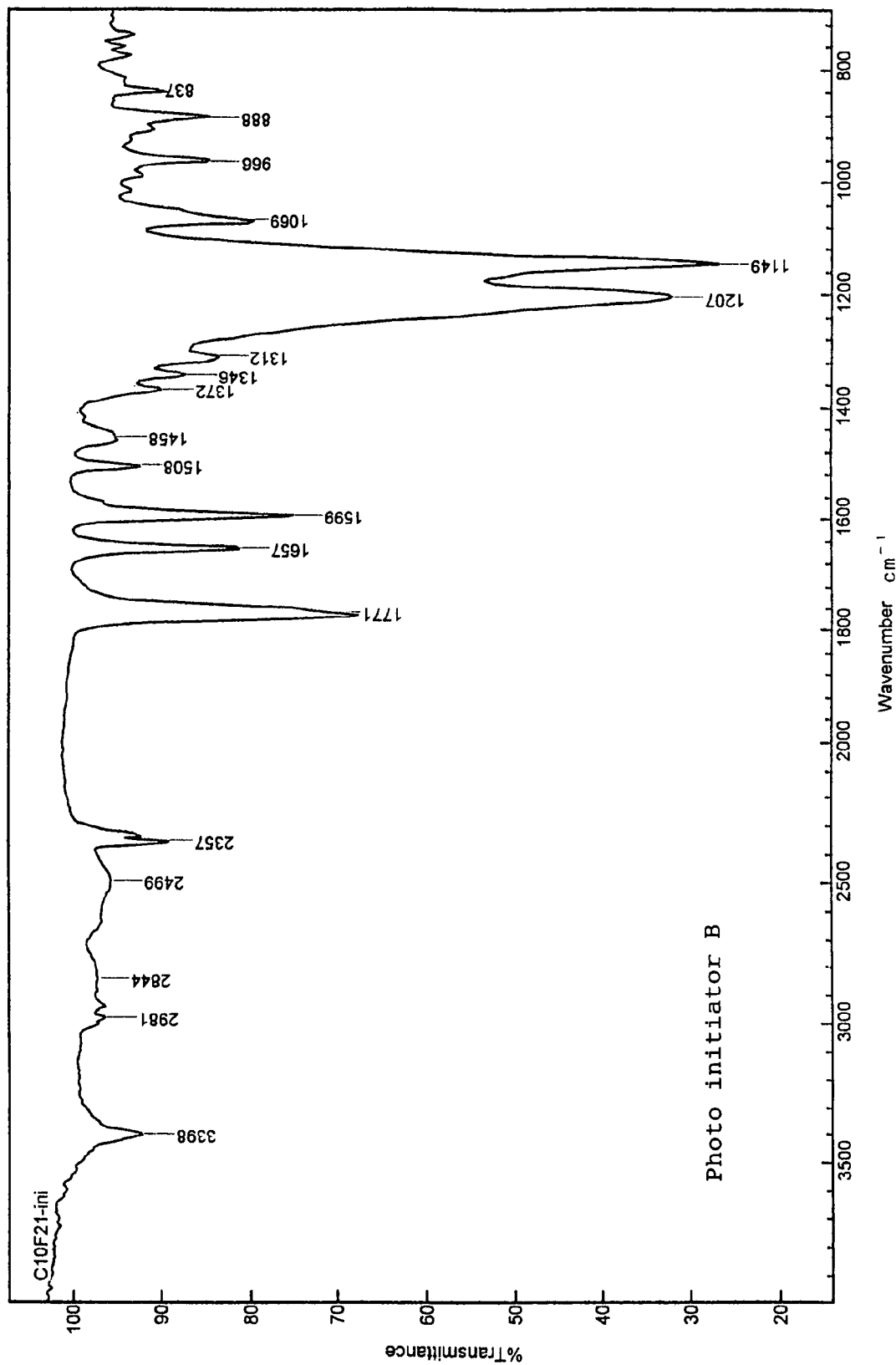
FIG. 3 is an IR chart of a fluorine-containing photo initiator B.

Identification Data on the Photo Initiator B:
IR (FIG. 3): O—H stretch at 3390–3500 cm$^{-1}$;
ester C=O stretch near 1770 cm$^{-1}$;
benzyl position C=O stretch near 1650 cm$^{-1}$;
benzene ring C=C stretch near 1600 cm$^{-1}$; and
perfluoroalkyl group C–F stretch near 1100–1200 cm$^{-1}$.

Example 3

Synthesis of Fluorine-Containing Photo Initiator C

A reaction was conducted in the same way as in Example 1 expect that 44 g of perfluoro-3,6,9-trioxatridecanoic acid (compound v in the following reaction equation) was used instead of 40 g of perfluorononanoic acid and the reaction temperature was set to 100° C. In this way, about 13 g of a transparent viscous liquid was obtained. This liquid was analyzed in the same way as in Example 1, so that it was identified that a target photo initiator C, 2-hydroxy-4'-[2-(perfluoro-3,6,9-trioxatridecanoyloxy) ethoxy]-2-methylpropiophenone was obtained as a main product. This liquid was used as the fluorine-containing photo initiator C in examples described hereinafter.

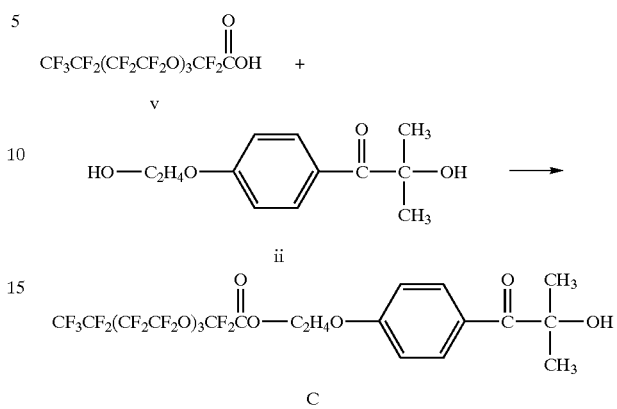

Example 4

Substrate with Composite Hard Coat Layer

An ultraviolet ray-curable hard coat agent (DESOLITE Z7503, manufactured by JSR Corp.) was applied onto a polycarbonate substrate (thickness: 0.6 mm, diameter: 12 cm) by spin coating. Thereafter, the resultant was heated at 60° C. in the atmosphere for 3 minutes, to remove the diluting solvent in the coat. In this way, a hard coat layer which had not been cured was formed. The above-mentioned hard coat agent was a composition containing a reactive inorganic filler, disclosed in Japanese Laid-open Patent Publication No. 9-100111 (1997).

Next, the following compounds were added to 99.4 parts by weight of a fluorine-containing solvent, FLUORINERT FC-77 (manufactured by Sumitomo 3M Ltd.), so as to prepare a surface material solution:

| | |
|---|---|
| perfluoropolyether diacrylate: (acryl-modified product of a Fomblin Z DOL manufactured by Ausimont Co., molecular weight: about 2,000), | 0.33 part by weight |
| 3-perfluorooctyl-2-hydroxypropyl acrylate: (manufactured by Daikin Fine Chemical laboratory Co.), and | 0.17 part by weight |
| fluorine-containing photo initiator A: | 0.1 part by weight. |

This surface material solution was applied onto the above-mentioned hard coat layer which had not been cured by spin coating. The resultant was dried at 60° C. for 3 minutes to form a surface layer which had not been cured.

Next, a high-pressure mercury lamp was used to radiate ultraviolet rays having an energy of 1,000 mJ/cm$^2$ onto the surface layer under nitrogen flow, thereby curing the hard coat layer and the surface layer simultaneously. The oxygen concentration in the ultraviolet ray radiation atmosphere was 80 ppm by volume. The thickness of the cured hard coat layer was 3.4 μm, and the thickness of the cured surface layer was about 30 nm. The thickness of the hard coat layer was measured with a stylus profilometer. The thickness of the surface layer was measured by X-ray fluorescence analysis (XRF), using perfluoropolyether (DEMNUM, manufactured by Daikin Industries, Ltd.) as a standard material. In this way, the substrate with the composite hard coat layer was obtained.

Example 5

Substrate with Composite Hard Coat Layer

A substrate with a composite hard coat layer was obtained in the same way as in Example 4 except that a surface material solution having the following composition was used. The thickness of the cured hard coat layer was 3.4 μm, and the thickness of the cured surface layer was about 30 nm.

| | |
|---|---|
| FLUORINERT FC-77: (manufactured by Sumitomo 3M Ltd.) | 99.4 parts by weight |
| perfluoropolyether diacrylate: (acryl-modified product of a Fomblin Z DOL manufactured by Ausimont Co., molecular weight: about 2,000) | 0.33 part by weight |
| 3-perfluorooctyl-2-hydroxypropyl acrylate: (manufactured by Daikin Fine Chemical Laboratory Co.) | 0.17 part by weight |
| fluorine-containing photo initiator B: | 0.1 part by weight |

Example 6

Substrate with Composite Hard Coat Layer

A substrate with a composite hard coat layer was obtained in the same way as in Example 4 except that a surface material solution having the following composition was used. The thickness of the cured hard coat layer was 3.4 μm, and the thickness of the cured surface layer was about 30 nm.

| | |
|---|---|
| FLUORINERT FC-77: (manufactured by Sumitomo 3M Ltd.) | 99.4 parts by weight |
| perfluoropolyether diacrylate: (acryl-modified product of a Fomblin Z DOL manufactured by Ausimont Co., molecular weight: about 2,000) | 0.5 part by weight |
| fluorine-containing photo initiator C: | 0.1 part by weight |

Comparative Example 1

A substrate with a composite hard coat layer was obtained in the same way as in Example 4 except that a surface material solution having the following composition was used. The thickness of the cured hard coat layer was 3.4 μm, and the thickness of the cured surface layer was about 30 nm.

| | |
|---|---|
| FLUORINERT FC-77: (manufactured by Sumitomo 3M Ltd.) | 99.5 parts by weight |
| perfluoropolyether diacrylate: (acryl-modified product of a Fomblin Z DOL manufactured by Ausimont Co., molecular weight: about 2,000) | 0.33 part by weight |
| 3-perfluorooctyl-2-hydroxypropyl acrylate: (manufactured by Daikin Fine Chemical laboratory Co.) | 0.17 part by weight |

Comparative Example 21

A substrate with a composite hard coat layer was obtained in the same way as in Comparative Example 1 except that an electron beam was radiated under nitrogen gas flow instead of the radiation of the ultraviolet rays under the nitrogen gas flow so as to cure the hard coat layer and the surface layer. A CURETRON (manufactured by NHV Corp.) was used as an electron beam radiating device, and the accelerating voltage of the electron beam and the radiation amount thereof were set to 200 kV and 5 Mrad, respectively. The oxygen concentration in the radiation atmosphere was 80 ppm by volume. The thickness of the cured hard coat layer was 3.4 μm, and the thickness of the cured surface layer was about 30 nm.

(Evaluation)

About the respective specimens produced in Examples 4 to 6 and Comparative Examples 1 and 2, the following performance tests were made.

(1) Abrasion Resistance

A steal wool #0000 was used, and the wool was reciprocated 20 times so as to be slid onto the hard coat surface of each of the specimens under a load of 4.9 N/cm². The degree of injuries generated at this time was judged with the naked eye. The criterion for the judgment was as follows:

○: No injuries were generated.
Δ: Injuries were slightly generated.
X: Injuries were generated.

(2) Water Repellency and Persistence thereof

About each of the specimens after it was allowed to stand at room temperature for one week from the production thereof, the contact angle of water to the composite hard coat layer surface was measured. The measurement was made before the specimen surface was slid with a cloth impregnated with a solvent and after the sliding. Conditions for the sliding were as follows: a nonwoven cloth (Bemcot Lint-free CT-8, manufactured by Asahi Kasei Co., Ltd.) was impregnated with acetone, and the fabric was reciprocated 50 times to be slid on the specimen surface under a load of 4.9 N/cm². The contact angle was measured at a temperature of 20° C. and a relative humidity of 60%, using a contact angle meter CA-D manufactured by Kyowa Interface Science Co., Ltd.

TABLE 1

| | | Contact angle (degrees) | |
|---|---|---|---|
| | Abrasion resistance | Before the sliding | After the sliding |
| Example 4 | ○ | 103.0 | 103.4 |
| Example 5 | ○ | 103.2 | 102.8 |
| Example 6 | ○ | 107.5 | 107.0 |
| Comparative Example 1 | ○ | 98.7 | 76.4 |
| Comparative Example 2 | ○ | 101.2 | 101.0 |

The results measured as described above are shown in Table 1.

As is clear from Table 1, the substrates of Examples 4 to 6, which each had the composite hard coat layer, had a very high abrasion resistance and an excellent water repellency and were very good in persistence thereof. The composite hard coat layers were not colored and were excellent in transparency. As is clear from comparison thereof with Comparative Example 2, the substrates of Example 4 to 6, which each had the composite hard coat layer, were not worse in all performances of abrasion resistance, contact angle and persistence thereof, and surface smoothness than the substrate having the composite hard coat layer obtained by the electron beam curing.

On the other hand, in Comparative Example 1, the surface material solution thereof contained no fluorine-containing photo initiator. Therefore, the contact angle thereof was remarkably reduced by the sliding of the cloth impregnated with acetone, and the persistence of the water repellency was not obtained. It appears that by the sliding the cloth, the fluorine-containing surface layer was wiped off so that the contact angle was made low.

Example 7

Optical Information Medium with Composite Hard Coat Layer

This example was a production example of an optical information medium with a composite hard coat layer (abbreviated to the optical disk). In this example, the produced optical disk was of a phase-change type. The present invention can be applied to various disks regardless of the kind of their recording layer. Thus, the present invention can be applied to not only this disk but also a read only type optical disk, a write once type optical disk or some other disk.

Figure 4:
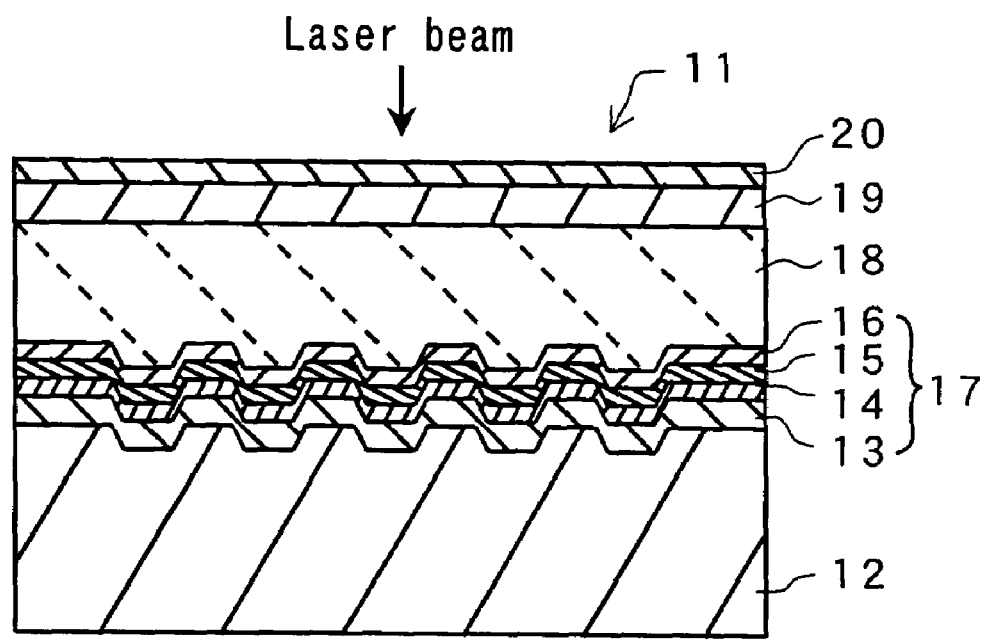
FIG. 4 is a schematic sectional view of an example of the optical disk with a composite hard coat layer of the present invention.

FIG. 4 is a schematic sectional view of an example of an optical disk with a composite hard coat layer. In FIG. 4, an optical disk 11 has, on a surface of a supporting substrate 12 in which fine concavity or convexity (such as information pits or pregrooves) are made, a reflecting layer 13, a second dielectric layer 14, a phase-change recording material layer 15, and a first dielectric layer 16 in this order. The disk 11 has a light-transmitting layer 18 on the first dielectric layer 16, and further has a hard coat layer 19 and a fluorine-containing surface layer 20 on the light-transmitting layer 18. In this example, the reflecting layer 13, the second dielectric layer 14, the phase-change recording material layer 15 and the first dielectric layer 16 constitute a recording layer 17. The combination of the hard coat layer 19 and the fluorine-containing surface layer 20 is referred to as the composite hard coat layer for the sake of convenience. The optical disk 11 is used in such a manner that a laser ray for recording or reproducing is radiated into the recording layer through the fluorine-containing surface layer 20, the hard coat layer 19 and the light-transmitting layer 18.

A sample of the optical disk having the layer structure illustrated in FIG. 4 was produced as follows.

The reflecting layer 13 made of $Al_{98}Pd_1Cu_1$ (atomic ratio) and having a thickness of 100 nm was formed on a surface of the disk-form supporting substrate 12 (made of polycarbonate, diameter: 120 mm, thickness: 1.1. mm), in which grooves for recording information were made, by sputtering. The depth of the grooves was λ/6 in an optical path length at wavelength λ=405 nm. The recording track pitch in a groove recording manner was set into 0.32 μm.

Next, a $Al_2O_3$ target was used to form the second dielectric layer 14 having a thickness of 20 nm on the surface of the reflecting layer 13 by sputtering. An alloy target made of a phase-change material was used to form the recording material layer 15 having a thickness of 12 nm on the surface of the second dielectric layer 14 by sputtering. The composition (atomic ratio) of the recording material layer 15 was set into $Sb_{74}Te_{18}(Ge_7In_1)$. A ZnS (80% by mole)-$SiO_2$ (20% by mole) target was used to form the first dielectric layer 16 having a thickness of 130 nm on the surface of the recording material layer 15 by sputtering.

Next, a radical-polymerizable ultraviolet ray-curable resin having the following composition was applied onto the surface of the first dielectric layer 16 by spin coating, and then ultraviolet rays were radiated thereon so as to form the light-transmitting layer 18 in such a manner that the thickness thereof would be 98 μm after the layer 18 was cured.

| (Composition of ultraviolet ray-curable resin for forming light-transmitting layer) | |
|---|---|
| urethane acrylate oligomer: (DIABEAM UK6035, manufactured by Mitsubishi Rayon Co., Ltd.) | 50 parts by weight |
| isocyanuric acid EO modified triacrylate: (ARONIX M315, manufactured by Toagosei Co., Ltd.) | 10 parts by weight |
| isocyanuric acid EO modified diacrylate: (ARONIX M215, manufactured by Toagosei Co., Ltd.) | 5 parts by weight |
| tetrahydrofurfuryl acrylate: | 25 parts by weight |
| photopolymerization initiator(1-hydroxycyclohexyl phenyl ketone): | 3 parts by weight |

Next, an ultraviolet ray/electron beam curing hard coat agent having the following composition was applied onto the light-transmitting layer 18 by spin coating, and then the resultant was heated at 60° C. in the atmosphere for 3 minutes to remove the diluting solvent in the coat. In this way, the hard coat layer 19 which had not been cured was formed.

| (Composition of hard coat agent) | |
|---|---|
| reactive group modified colloidal silica: (dispersing medium: propylene glycol monomethyl ether acetate, nonvolatile content: 40% by weight) | 100 parts by weight |
| dipentaerythritol hexaacrylate: | 48 parts by weight |
| tetrahydrofurfuryl acrylate: | 12 parts by weight |
| propylene glycol monomethyl ether acetate: (non-reactive diluting solvent) | 40 parts by weight |
| IRGACURE 184 (polymerization initiator): | 5 parts by weight |

Next, the following compounds were added to 99.7 parts by weight of a fluorine-containing solvent, FLORINARE FC-77 (manufactured by Sumitomo 3M Ltd.), so as to prepare a surface material solution:

| | |
|---|---|
| perfluoropolyether diacrylate: (acryl-modified product of a Fomblin Z DOL manufactured by Ausimont Co., molecular weight: about 2,000), | 0.06 part by weight |
| 3-perfluorooctyl-2-hydroxypropyl acrylate: (manufactured by Daikin Fine Chemical laboratory Co.), and | 0.19 part by weight |
| fluorine-containing photo initiator C: | 0.05 part by weight. |

This surface material solution was applied onto the above-mentioned hard coat layer 19 which had not been cured by spin coating. The resultant was dried at 60° C. for 3 minutes to form the surface layer 20 which had not been cured.

Next, a high-pressure mercury lamp was used to radiate ultraviolet rays having an energy of 1000 mJ/cm² onto the surface layer 19 under nitrogen flow, thereby curing the hard coat layer 19 and the surface layer 20 simultaneously. The oxygen concentration in the ultraviolet ray radiation atmosphere was 80 ppm by volume. The thickness of the cured hard coat layer 19 was 2.5 82 m, and the thickness of the cured surface layer 20 was about 28 nm. In this way, an optical recording disk sample No. 1 with the composite hard coat layer was obtained.

(Evaluation)

An optical disk evaluating device (DDU-1,000, manufactured by Pulstec Industrial Co., Ltd.) was used to evluate the recording/reproducing property of the produced optical recording disk sample No. 1 under the following conditions:

| laser wavelength: | 405 nm, |
|---|---|
| objective lens numerical aperture NA: | 0.85, |
| linear velocity: | 6.5 m/s, |
| recording signals: | |
| 1–7 modulating signals (shortest signal length: 2T), and recording area: | groove recording. |

(1) Abrasion Resistance

Random signals were recorded at a position 40 mm apart in the radius direction from the center of the optical recording disk sample. The initial jitter value thereof was then measured. Next, a steel wool #0000 was reciprocated 20 times so as to be slid on the surface of the composite hard coat of the disk under a load of 2.5 N/cm$^2$. Thereafter, the jitter value (jitter value after the test) was again measured. The direction in which the steel wool was slid was made into the radius direction of the disk, and the used steel wool had a size of 1.0 cm×1.0 cm.

(2) Anti-Staining Property

Random signals were recorded at a position 40 mm apart in the radius direction from the center of the optical recording disk sample. The initial jitter value thereof was then measured. Next, a middle finger was pushed against a position of the hard coat side surface of the disk 40 mm apart in the radius direction from the center of the disk at a pushing force of 9.8 N for 10 seconds. In the way, the fingerprint was adhered thereon. Thereafter, 8 pieces from a commercially available facial tissue (manufactured by Crecia Corp.), which were in layers, were used to wipe off the disk slowly from the inner circumference thereof to the outer circumference so as to remove the fingerprint. The pushing force at the time of the wiping off was set into 4.9 N/cm$^2$, and the number of the wiping operation(s) was set into one. Thereafter, the jitter value (jitter value after the test) was again measured.

TABLE 2

| | | Jitter value (%) | |
|---|---|---|---|
| | | Initial | After the test |
| Optical recording disk sample No. 1 | Abrasion resistance | 7.6 | 7.6 |
| | Anti-staining property | 7.6 | 7.8 |

Results of the above-mentioned measurements are shown in Table 2.

As is clear from Table 2, the optical recording disk sample No. 1 was excellent in the initial jitter value and the jitter value after both of the abrasion resistance test and anti-staining test. The composite hard coat layer thereof was not colored and the transparency thereof was very good.

Example 8

Lens with Fluorine-Containing Surface Layer

In this example, a fluorinate-containing surface layer was given on the surface of spherical lens of 100 80 mm produced by injection molding from polycarbonate.

Corona discharge device (3005DW-SLR, SOFTAL JAPAN Co., Ltd.) was used to radiate a 400 W·min/m$^2$ of energy on the both surfaces of the spherical lens, thereby performing the treatment for hydrophilization. Next, 0.3% by weight 3-acryloxypropyltrimethoxysilane (silane coupling agent, KBM-5103, Shin-Etsu Chemical Co., Ltd.) solution in isopropanol was applied to the both surfaces of the lens by dipping method. The lens was stood in darkroom at room temperature overnight. Thereafter, the surface material solution of the following composition was applied to the both surfaces of the lens, and dried at 60° C. for 3 min so as to form an uncured surface layer. The treatment by silane coupling agent was performed to improve the adhesion between the lens surface and the surface layer.

| (Composition of surface material solution) | | |
|---|---|---|
| fluorine-containing solvent FLUORINERT FC-77: (manufactured by Sumitomo 3M Ltd.) | 99.4 | parts by weight |
| perfluoropolyether diacrylate: (acryl-modified product of a Fomblin Z DOL manufactured by Ausimont Co., molecular weight: about 2,000) | 0.33 | part by weight |
| 3-perfluorooctyl-2-hydroxypropyl acrylate: (manufactured by Daikin Fine Chemical laboratory Co.) | 0.17 | part by weight |
| fluorine-containing photo initiator C: | 0.1 | part by weight |

Next, a high-pressure mercury lamp was used to radiate ultraviolet rays having an energy of 1,000 mJ/cm$^2$ onto the surface layer under nitrogen flow, thereby curing the surface layers. The oxygen concentration in the ultraviolet ray radiation atmosphere was 80 ppm by volume. Thereafter, the lens was heated at 60° C. for 24 hours in order to fix silane coupling agent. The thickness of the cured surface layer was about 30 nm. In this way, the lens with fluorine-containing surface layers on the both surfaces thereof was obtained.

(Evaluation: Water Repellency and Persistence thereof)

About the specimen of the lens after it was allowed to stand at room temperature for one week from the production thereof, the water repellency and persistence thereof of the lens surface was measured in the same evaluation way as in Examples 4 to 6. The water angle of the lens surface before the sliding is 103.3°, and the water angle of the lens surface after the sliding by use of a nonwoven cloth impregnated with acetone is 102.4°. The lens surface was not colored and were excellent in transparency. It was cleared that according to the use or material of an article, fluorine-containing surface layer excellent in anti-staining property and persistence thereof can be formed by using the surface layer material of the present invention.

In the above-mentioned examples 4 to 6, the composite hard coat layer was given on the polycarbonate substrate. In the above-mentioned example 7, the composite hard coat layer was given to the phase-change type optical disks. However, the present invention can be applied to read only type optical disks or write once type optical disks as well as optical disks having a phase-change type recording layer. The present invention can also be applied to not only optical information media but also optical lens, optical filters, anti-reflection films, and various display elements. Therefore, the above-mentioned working examples are merely examples in all points, and the present invention should not be restrictedly interpreted by the examples. Furthermore, all modifications belonging to a scope equivalent to that of the claims are within the scope of the present invention.

What is claimed is:

1. A fluorine-containing acetophenone derivative represented by the following general formula (I):

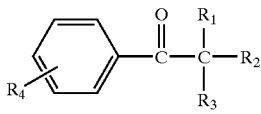

wherein $R_1$, $R_2$ and $R_3$ each independently represent an organic group other than aryl group, or a hydroxyl group; and any two of $R_1$, $R_2$ and $R_3$ may be linked to each other to form a ring, and $R_4$ represents a fluorine-containing organic group, wherein in the general formula (I), the organic groups represented by $R_1$, $R_2$ and $R_3$, none of which are aryl groups, are alkyl groups which may be substituted, alkoxy groups which may be substituted, alkylcarbonyloxy groups which may be substituted, arylcarbonyloxy groups which may be substituted or amino groups.

2. A surface layer material, comprising:
a fluorine-containing (meth)acrylate compound, and
a fluorine-containing acetophenone derivative as a photo initiator represented by the following general formula (I):

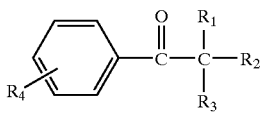

wherein $R_1$, $R_2$ and $R_3$ each independently represent an organic group other than aryl group, or a hydroxyl group; and any two of $R_1$, $R_2$ and $R_3$ may be linked to each other to form a ring, and $R_4$ represents a fluorine-containing organic group, wherein in the general formula (I), the organic groups represented by $R_1$, $R_2$ and $R_3$ none of which are aryl groups, are alkyl groups which may be substituted, alkoxy groups which may be substituted, alkylcarbonyloxy groups which may be substituted, arylcarbonyloxy groups which may be substituted or amino groups.

3. An article with a composite hard coat layer, comprising:
a hard coat layer on a surface of the article, and
a fluorine-containing surface layer on a surface of the hard coat layer,
wherein
the hard coat layer is made of a cured product of a hard coat agent composition comprising an active energy ray-curable compound, and
the fluorine-containing surface layer is made of a cured product of a surface layer material comprising a fluorine-containing (meth)acrylate compound and a fluorine-containing acetophenone derivative as a photo initiator represented by the following general formula (I):

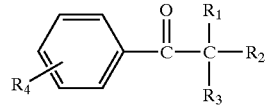

wherein $R_1$, $R_2$ and $R_3$ each independently represent an organic group other than aryl group, or a hydroxyl group; and any two of $R_1$, $R_2$ and $R_3$ may be linked to each other to form a ring, and $R_4$ represents a fluorine-containing organic group, wherein in the general formula (I), the organic groups represented by $R_1$, $R_2$ and $R_3$, none of which are aryl groups, are alkyl groups which may be substituted, alkoxy groups which may be substituted, alkylcarbonyloxy groups which may be substituted, arylcarbonyloxy groups which may be substituted or amino groups.

4. The article with the composite hard coat layer according to 3, wherein the fluorine-containing surface layer has a thickness of 1 nm or more and 100 nm or less.

5. The article with the composite hard coat layer according to 3, wherein the active energy ray-curable compound comprised in the hard coat agent composition is a compound having at least one reactive group selected from the group consisting of a (meth)acryloyl group, a vinyl group and a mercapto group.

6. The article with the composite hard coat layer according to 3, wherein the hard coat agent composition comprises a photo initiator and optionally comprises an inorganic filler.

7. The article with the composite hard coat layer according to any one of claims 3 to 6, the article being an optical recording medium, a magneto-optical recording medium, an optical lens, an optical filter, an anti-reflection film, or any one of various display elements.

8. A method for forming a composite hard coat layer comprising a hard coat layer on a surface of an article and a fluorine-containing surface layer, the method comprising:
applying a hard coat agent composition comprising an active energy ray-curable compound onto a surface of an article to be hard-coat-treated, thereby forming a hard coat agent composition layer,
applying, onto the surface of the hard coat agent composition layer, a surface layer material comprising a fluorine-containing (meth)acrylate compound and a fluorine-containing acetophenone derivative as a photo initiator represented by the following general formula (I):

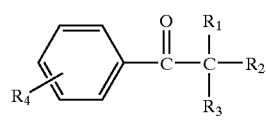

wherein $R_1$, $R_2$ and $R_3$ each independently represent an organic group other than aryl group, or a hydroxyl group; and any two of $R_1$, $R_2$ and $R_3$ may be linked to each other to form a ring, and $R_4$ represents a fluorine-containing organic group, wherein in the general formula (I), the organic groups represented by $R_1$, $R_2$ and $R_3$, none of which are aryl groups, are alkyl groups which may be substituted, alkoxy groups which may be substituted, alkylcarbonyloxy groups which may be substituted, arylcarbonyloxy groups which may be substituted or amino groups.

9. The method for forming the composite hard coat layer according to claim 8, wherein after the hard coat agent composition is applied onto the surface of the article, thereby forming the hard coat agent composition layer, the hard coat agent composition layer is dried to remove a solvent contained in the hard coat agent composition from the hard coat agent composition layer, and subsequently the surface layer material is applied onto the surface of the hard coat agent composition layer, thereby forming the surface material layer.

10. The method for forming the composite hard coat layer according to claim 8, wherein at the time of applying the surface layer material, there is used, as a solvent, a solvent in which the active energy ray-curable compound in the already-formed hard coat agent composition layer is not substantially dissolved.

11. The method for forming the composite hard coat layer according to claim 8, wherein the ultraviolet rays are radiated in an atmosphere having a oxygen concentration of 500 ppm by volume or less.

12. An article with a fluorine-containing surface layer made of a cured product of a surface layer material on a surface of the article, wherein the surface layer material comprises a fluorine-containing (meth)acrylate compound and a fluorine-containing acetophenone derivatives as a photo initiator represented by the following general formula (I):

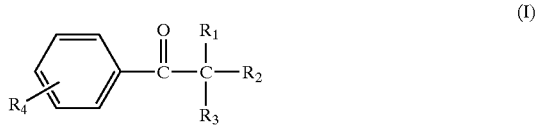

wherein $R_1$, $R_2$ and $R_3$ each independently represent an organic group other than aryl group, or a hydroxyl group; and any two of $R_1$, $R_2$ and $R_3$ may be linked to each other to form a ring, and $R_4$ represents a fluorine-containing organic group, wherein in the general formula (I), the organic groups represented by $R_1$, $R_2$ and $R_3$, none of which are aryl groups, are alkyl groups which may be substituted, alkoxy groups which may be substituted, alkylcarbonyloxy groups which may be substituted, arylcarbonyloxy groups which may be substituted or amino groups.

13. The fluorine-containing acetophenone derivative according to claim 1, wherein the fluorine-containing organic group of $R_4$ in the general formula (I) is selected from the group consisting of
(a) —[C(X)F]k-;
(b) —[C(X)F—O]l-;
(c) —[C(X)F—C(Y)F—O]m-; and
(d) —[C(X)F—C(Y)F—C(Z)F—O]n-,
wherein
X, Y and Z each independently represent a F atom or a $CF_3$ group, and
k, l, m and n each represent the number of the fluorine-containing units, in such a manner that the total number of the fluorinated carbon atoms contained in the selected fluorine-containing unit is 5 or more.

14. The fluorine-containing acetophenone derivative according to claim 13, wherein the fluorine-containing organic group represented by $R_4$ in the general formula (I) is an Rfa-L- group, where L represents a bivalent linking group, having a perfluoroalkyl group Rfa containing the fluorine-containing unit (a) —[C(X)F]k- (5≦k).

15. The fluorine-containing acetophenone derivative according to claim 13, wherein the fluorine-containing organic group represented by $R_4$ in the general formula (I) is an Rfa-COO—$(CH_2)$j-O— group, where j is an integer of 2 to 6, or Rfa-NHCOO—$(CH_2)$j-O— group, where j is an integer of 2 to 6, having a perfluoroalkyl group Rfa containing the fluorine-containing unit (a) —[C(X)F]k- (5≦k).

16. The fluorine-containing acetophenone derivative according to claim 13, wherein the fluorine-containing organic group represented by $R_4$ in the general formula (I) is an Rfe-L- group, where L represents a bivalent linking group, having a perfluoroether-containing group Rfe containing at least one selected from the group consisting of the fluorine-containing units (b) —[C(X)F—O]l-, (c) —[C(X)F—C(Y)F—O]m-, and (d) —[C(X)F—C(Y)F—C(Z)F—O]n-.

17. The fluorine-containing acetophenone derivative according to claim 13, wherein the fluorine-containing organic group represented by $R_4$ in the general formula (I) is an Rfe-COO—$(CH_2)$j-O— group, where j is an integer of 2 to 6, or Rfe-NHCOO—$(CH_2)$j-O— group, where j is an integer of 2 to 6, having a perfluoroether-containing group Rfe containing at least one selected from the group consisting of the fluorine-containing units (b) —[C(X)F—O]l-, (c) —[C(X)F—C(Y)F—O]m-, and (d) —[C(X)F—C(Y)F—C(Z)F—O]n-.

* * * * *